US006362000B1

(12) United States Patent
Kappes et al.

(10) Patent No.: US 6,362,000 B1
(45) Date of Patent: *Mar. 26, 2002

(54) FUSION PROTEIN DELIVERY SYSTEM AND USES THEREOF

(75) Inventors: John Christopher Kappes; Xiaoyun Wu, both of Birmingham, AL (US)

(73) Assignee: University of Alabama Research Foundation, Birmingham, AL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/434,743

(22) Filed: Nov. 5, 1999

Related U.S. Application Data

(62) Division of application No. 08/947,516, filed on Sep. 29, 1997, now Pat. No. 6,001,985, which is a continuation of application No. 08/421,982, filed on Apr. 14, 1995, now abandoned.

(51) Int. Cl.$^7$ .............................................. C12N 15/86
(52) U.S. Cl. ..................... 435/456; 435/455; 435/457; 435/320.1; 536/23.1; 536/23.4
(58) Field of Search .............................. 536/23.4, 23.1; 435/320.1, 455, 456, 457

(56) References Cited

U.S. PATENT DOCUMENTS

| 5,175,099 A | 12/1992 | Willis |
| 5,378,806 A | 1/1995 | Willis |
| 5,665,577 A | 9/1997 | Sodroski |
| 5,861,161 A | 1/1999 | Cohen |
| 5,981,276 A | 11/1999 | Sodroski |
| 6,043,081 A | * 3/2000 | Cohen et al. ............. 435/320.1 |

FOREIGN PATENT DOCUMENTS

| DE | 275259 | 1/1990 |
| EP | 356021 | 2/1990 |
| WO | 90/15875 | 12/1990 |
| WO | 92/00987 | 1/1992 |
| WO | 93/24632 | 9/1993 |
| WO | 93/25235 | 12/1993 |
| WO | 94/17825 | 8/1994 |
| WO | 95/16705 | 6/1995 |
| WO | 95/26361 | 10/1995 |
| WO | 96/07741 | 3/1996 |
| WO | 96/11696 | 4/1996 |
| WO | 97/36481 | 10/1997 |

OTHER PUBLICATIONS

Paxton et al. Journal of Virology. vol. 67(12): 7229–7237, Dec. 1993.*

Huang et al. (1995) "p6$^{Gag}$ Is Required for Particle Production from Full–Length Human Immunodeficiency Virus Type 1 Molecular Clones Expressing Protease" *J. Virol.* 69(*11*):6810–6818.

Schumann et al. (1996) "Therapeutic Effect of Gag–Nuclease Fusion Protein on Retrovirus–Infected Cell Cultures" *J. Virol.* 70(7):4329–4337.

Akari et al., "Biological characterization of human immunodeficiency virus type 1 and type 2 mutants in human peripheral blood mononuclear cells," *Arch. Virol.* 123:157–167 (1992).

Alton et al., "Nucleotide sequence analysis of the chloramphenicol resistance transposon Tn9," *Nature* 282:864–869 (1979).

Balotta et al., "Antisense Phosphorothioate Oligodeoxynucleotides Targeted to the vpr Gene Ingibit Human Immunodeficiency Virus Type 1 Replication in Primary Human Macrophages," *J. Virol.* 67(7):4409–4414 (1993).

Cohen et al., "Human Immunodeficiency Virus vpr Product Is a Virion–Associated Regulatory Protein," *J. Virol.* 64(6):3097–3099 (1990).

Cohen et al., "Identification of HIV–1 vpr Product and Function," *J. Acq. Immune Def. Synd.* 3:11–18 (1990).

Dedera et al., "Viral Protein R of Human Immunodeficiency Virus Types 1 and 2 Is Dispensable for Replication and Cytopathogenicity in Lymphoid Cells," *J. Virol.* 63(7):3205–3208 (1989).

Desrosiers. "HIV with Multiple Gene Deletions as a Live Attenuated Vaccine for AIDS," *AIDS Research and Human Retroviruses* 8(3):411–421 (1992).

Di Marzio et al., "Mutational Analysis of Cell Cycle Arrest, Nuclear Localization, and Virion Packaging of Human Immunodeficiency Virus Type 1 Vpr," *J Virol.* 69(12):7909–7916 (1995).

Gibbs et al., "Construction and In Vitro Properties of SIV$_{mac}$ Mutants with Deletions in "Nonessential" Genes," *AIDS Research and Human Retroviruses* 10(5):607–616 (1994).

Gibbs et al., "Progression to AIDS in the Absence of a Gene for vpr or vpx," *J. Virol.* 69(4):2378–2383 (1995).

Guyader et al., "VPX mutants of HIV–2 are infectious in established cell lines but display a severe defect in peripheral blood lymphocytes," *The EMBO Journal* 8(4):1169–1175 (1989).

(List continued on next page.)

*Primary Examiner*—Remy Yucel
(74) *Attorney, Agent, or Firm*—Alston & Bird LLP

(57) ABSTRACT

The present invention provides a composition of matter, comprising: DNA encoding a viral Vpx protein fused to DNA encoding a protein. In another embodiment of the present invention, there is provided a composition of matter, comprising: DNA encoding a viral Vpr protein fused to DNA encoding a protein. The present invention further provides DNA, vectors and methods for expressing a lentiviral pol gene in trans, independent of the lentiviral gag-pol. A gene transduction element is optionally delivered to a lentiviral vector according to the present invention. Also provided are various methods of delivering a virus inhibitory molecule to a target in an animal. Further provided is a pharmaceutical composition.

23 Claims, 14 Drawing Sheets

OTHER PUBLICATIONS

Hattori et al., "The human immunodeficiency virus type 2 vpr gene is essential for productive infection of human macrophages," *Proc. Natl. Acad. Sci. USA* 87:8080–8084 (1990).

He et al., "Human Immunodeficiency Virus Type 1 Viral Protein R (Vpr) Arrests Cells in the $G_2$ Phase of the Cell Cycle by Inhibiting $p34^{cdc2}$ Activity," *J. Virol.* 69(11):6705–6711 (1995).

Heinzinger et al., "The Vpr protein of human immunodeficiency virus type 1 influences nuclear localization of viral nucleic acids in nondividing host cells," *Proc. Natl. Acad. Sci. USA* 91:7311–7315 (1994).

Hoch et al., "vpr Deletion Mutant of Simian Immunodeficiency Virus Induces AIDS in Rhesus Mondeys," *J. Virol.* 69(8):4807–4813 (1995).

Horton et al., "HIV–2 Viral Protein X Association with the Gag p27 Capsid Protein," *Virology* 199:453–457 (1994).

Hu et al., "Analysis and function of viral protein X (VPX) of HIV–2", *Virol.* 173:624–630 (1989).

Kappes et al., "Human Immunodeficiency Virus Type 2 vpx Protein Augments Viral Infectivity," *Virology* 184:197–209 (1991).

Kappes et al., "Identification of a Novel Retroviral Gene Unique to Human Immunodeficiency Virus Type 2 And Simian Immunodeficiency Virus $SIV_{MAC}$," *J. Virol.* 62(9):3501–3505 (1988).

Kappes et al., "Intracellular Transport And Virion Incorporation of vpx Requires Interaction With Other Virus Type–Specific Components," *J. Virol.* 193:222–223 (1993).

Kappes et al., "Targeting foreign proteins to HIV particles via fusion with Vpr and Vpx", *J. Biol. Chem.* Suppl. 21(A):395, Ref. No. C6–326 (1994).

Kappes et al., "The HIV Vpx and Vpr genes mediate virion incorporation of nuclease fusion proteins," *J. Biol. Chem.* Suppl. 21(A):162, Ref. No. J513 (1995).

Kewalramani et al., "Protein Stability Influences Human Immunodeficiency Virus Type 2 Vpr Virion Incorporation and Cell Cycle Effect," *Virology* 218:326–334 (1996).

Kewalramani et al., "Vpx Assocation with Mature Core Structures of HIV–2," *Virology* 218:159–168 (1996).

Kirchhoff et al., "Upstream U3 Sequences in Simian Immunodeficiency Virus Are Selectively Deleted In Vivo in the Absence of an Intact nef Gene," *J. Virol.* 68(3):2031–2037 (1994).

Kondo et al., "The $p6^{gag}$ domain of Human Immunodeficiency Virus Type 1 Is Sufficient for the Incorporation of Vpr into Heterologous Viral Particles," *J. Virol.* 69(5):2759–2764 (1995).

Lang et al., "Importance of vpr for Infection of Rhesus Monkeys with Simian Immunodeficiency Virus," *J. Virol.* 67(2):902–912 (1993).

Lavallee et al., "Requirement of the $Pr55^{gag}$ Precursor for Incorporation of the Vpr Product into Human Immunodeficiency Virus Type 1 Viral Particles," *J. Virol.* 68(3):1926–1934 (1994).

Lee et al., "The Role of vpx in the life cycle of HIV–2," submitted to the Proceedings of the Third Annual "Colloque Des Cent Gardes" (1988).

Levy et al., "Extracellular Vpr Protein Increases Cellular Permissiveness to Human Immunodeficiency Virus Replication and Reactivates Virus from Latency," *J. Virol.* 69(2):1243–1252 (1995).

Levy et al., "Induction of Cell Differenctiation by Human Immunodeficiency Virus 1 vpr," *Cell* 72:541–550 (1993).

Levy et al., "Serum Vpr regulates productive infection and latency of human immunodeficiency virus type 1," *Proc. Natl. Acad. Sci. USA* 91:10873–10877 (1994).

Liu et al., "Incorporation Of Functional Human Immunodeficiency Virus Type 1 Integrase Into Virions Independent Of The Gag/Pol Precursor Protein," (Revised Manuscript, #JVI 548–97) *J. Virology* 71:7704–7710 (1997).

Lu et al., "A Leucine Triplet Repeat Sequence $(LXX)_4$ in $p6^{gag}$ IsImportant for Vpr Incorporation into Human Immunodeficiency Virus Type 1 Particles," *J. Virol.* 69(11):6873–6879 (1995).

Lu et al., "Human Immunodeficiency Virus Type 1 Viral Protein R Localization in Infected Cells and Virions," *J. Virol.* 67(11):6542–6550 (1993).

Macreadie et al., "A domain of human immunodeficiency virus type 1 Vpr containing repeated H(S/F)RIG amino acid motifs causes cell growth arrest and structural defects," *Proc. Natl. Acad. Sci. USA* 92:2770–2774 (1995).

Mahalingam et al., "Functional Analysis of HIV–1 Vpr: Identification of Determinants Essential for Subcellular Localization," *Virology* 212:331–339 (1995).

Mahalingam et al., "HIV–1 Vpr interacts with a human 34–kDa mov34 homologue, a cellular factor linked to the $G_2/M$ phase transition of the mammalian cell cycle," *Proc. Natl. Acad. Sci. USA* 95:3419–3424 (1998).

Mahalingam et al., "Identification of Residues in the N–Terminal Acidic Domain of HIV–1 Vpr Essential for Virion Incorporation," *Virology* 207:297–302 (1995).

Mahalingam et al., "The Carboxy–Terminal Domain Is Essential for Stability and Not for Virion Incorporation of HIV–1 Vpr into Virus Particles," *Virology* 214:647–652 (1995).

Marcon et al., "Dispensable Role of the Human Immunodeficiency Virus Type 2 Vpx Protein in Viral Replication," *J. Virol.* 65(7):3938–3942 (1991).

Marcon et al., "Functional Studies of the HIV–2 *VPX* Protein," p. 310 (Abstract).

Matsuda et al., "A virion–specific inhibitory molecule with therapeutic potential for human immunodeficiency virus type 1," *Proc. Natl. Acad. Sci. USA* 90:3544–3548 (1993).

Natsoulis and Boeke, "New antiviral strategy using capsid–nuclease fusion proteins," *Nature* 352:632–635 (1991).

Natsoulis et al., "Targeting of a nuclease to murine leukemia virus capsids inhibits viral multiplication," *Proc. Natl. Acad. Sci. USA* 92:364–368 (1995).

Ogawa et al., "Mutational analysis of the Human Immunodeficiency Virus vpr Open Reading Frame," *J. Virol.* 63(9):4110–4114 (1989).

Orkin et al., "Report And Recommendations Of The Panel To Assess The NIH Investment In Research On Gene Therapy," NIH Panel Report. Dec. 1995. Entire Report.

Park et al., "Amino Acid Sequence Requirements for the Incorporation of the Vpx Protein of Simian Immunodeficiency Virus into Virion Particles," *J. Acq. Immune Def. Synd.* 10:506–510 (1995).

Park et al., "Targeting a foreign protein into virion particles by fusion with the Vpx protein of Simian Immunodeficiency Virus," *J. Acq. Immune Def. Synd.* 11(4):341–50 (1996).

Paxton et al., "Incorporation of Vpr into Human Immunodeficiency Virus Type 1 Virion: Requirement for the p6 Region of gag and Mutational Analysis," *J. Virol.* 67(12):7229–7237 (1993).

Percy et al., "A poliovirus replicon containing the chloramphericol acetyltransferase gene can be used to study the replication and encapsidation of poliovirus RNA", *J. Virol.* 66(8):5040–5046 (1992).

Re et al., "Human Immunodeficiency Virus Type 1 Vpr Arrests the Cell Cycle in $G_2$ by Inhibiting the Activation of p34$^{cdc2}$–Cyclin B," *J. Virol.* 69(11):6859–6864 (1995).

Rogel et al., "The Human Immunodeficiency Virus Type 1 vpr Gene Prevents Cell Proliferation during Chronic Infection," *J. Virol.* 69(2):882–888 (1995).

Sato et al., "Targeting of Chrolamphenicol Acetyltransferase to Human Immunodeficiency Virus Particles via Vpr and Vpx," *Microbiol. Immunol.* 39(12):1015–1019 (1995).

Shibata et al., "Construction and Characterization of an Infectious DNA Clone and of Mutants of Simian Immunodeficiency Virus Isolated from the African Green Monkey," *J. Virol.* 64(1):307–312 (1990).

Shibata et al., "Generation of a Chimeric Human and Simian Immunodeficiency Virus Infectios to Monkey Peripheral Blood Mononuclear Cells," *J. Virol.* 65(7):3514–3520 (1991).

Shibata et al., "Mutational Analysis of the Human Immunodeficiency Virus Type 2 (HIV–2) Genome in Relation to HIV–1 and Simian Immunodeficiency Virus $SIV_{AGM}$," *J. Virol.* 64(2):742–747 (1990).

Smith et al., "Single–step purification of polypeptides expressed in *Escherichia coli* as fusions with glutathione S–transferase," *Gene* 67:31–40 (1988).

Tristem et al., "Evolution Of The Primate Lentiviruses: Evidence From Vpx And Vpr," *EMBO J.* 11:3405–3412 (1992).

Tristem et al., "Origin Of Vpx In Lentiviruses," *Nature* 347:341–342.39 (1990).

Trono et al., "HIV Accessory Proteins: Leading Roles for the Supporting Cast," *Cell* 82:189–192 (1995).

Wang et al., "Particle assembly and Vpr expression in human immunodeficiency virus type 1–infected cells demonstrated by immunoelectron microscopy," *Journal of General Virology* 75:2607–2614 (1994).

Westervelt et al., "Dual Regulation of Silent and Productive Infection in Monocytes by Distinct Human Immunodeficiency Virus Type 1 Determinants," *J. Virol.* 66(6):3925–3931 (1992).

Wong–Staal et al., "Human Immunodeficiency Virus: The Eighth Gene," Aids Research and Human Retroviruses 3(1): (1987).

Wu et al., "Functional RT And IN Incorporated Into HIV–1 Particles Independent Of The Gag/Pol Precursor Protein," *EMBO J* 16:0, 101–109 (1997).

Wu et al., "Functional RT And IN Incorporated Into HIV–1 Particles Independent Of The Gag/Pol Precursor Protein," *EMBO J* 16(16):5113–5122 (1997).

Wu et al., "HIV/SIV Virion Associated Accessory Genes Mediate Efficient Packaging Of Nuclease Fusion Proteins Into The Virus Particle," The First National Conference on Human Retroviruses and Related Infections, Washington, D.C. (1993).

Wu et al., "Inhibition of Human And Simian Immunodeficiency Virus Protease Function By Targeting Vpx–Protease––Mutant Fusion Protein Into Viral Particles," *J. Virol.* 3378–3384 (1996).

Wu et al., "Localization of the Vpx Packaging Signal within the C Terminus of the Human Immunodeficiency Virus Type 2 Gag Precursor Protein," *J. Virol.* 68(10):6161–6169 (1994).

Wu et al., "Targeting foreign Proteins To Human Immunodeficiency Virus Particles Via Fusion With Vpr And Vpx," (Revised Manuscript, #JV1 1529–94),*J. Virology* 69:3389–3398 (1995).

Wu et al., "Targeting foreign proteins to human immunodefieciency viruses types 1 and 2 via fusion with Vpr and Vpx", *Biol. Abstr./RRM* 47(4):MT–323, Ref No. 66007 (1995).

Wu et al., "Multiple Glycoproteins Synthesized by the Smallest RNA Segment (S10) of Bluetongue Virus," *J. Virol.* 66:7104–7112 (1992).

Yao et al., "Mutagenic Analysis of Human Immunodeficiency Virus Type 1 Vpr: Role of a Predicted N–Terminal Alpha–Helical Structure in Vpr Nuclear Localization and Virion Incorporation," *J. Virol.* 69(11):7032–7044 (1995).

Yu et al., "Open Reading Frame vpr of Simian Immunodeficiency Virus Encodes a Virion–Associated Protein," *J. Virol.* 64(11):5688–5693 (1990).

Yu et al., "The vpx gene of Simian Immunodeficiency Virus Facilitates Efficient Viral Replication in Fresh Lymphocytes and Macrophages," *J. Virol.* 65(9):5088–5091 (1991).

Yu et al., "Vpx of Simian Immunodeficiency Virus Is Localized Primarily Outside the Virus Core in Mature Virions," *J. Virol.* 67(7):4386–4390 (1993).

Yuan et al., "Human Immunodeficiency Virus vpr Gene Encodes a Virion–Associated Protein," *Aids Research and Human Retroviruses* 6(11):1265–1271 (1990).

Zhao et al., "Biochem. Mechanism of HIV–1 Vpr function", *J. Biol. Chem.* 269:15577–15582 (1994).

Zhao et al., "Biochemical Mechanism of HIV–1 Vpr Function: Oligomerization Mediated by the N–Terminal Domain," *J. Biol. Chem.* 269:32131–32137 (1994).

* cited by examiner

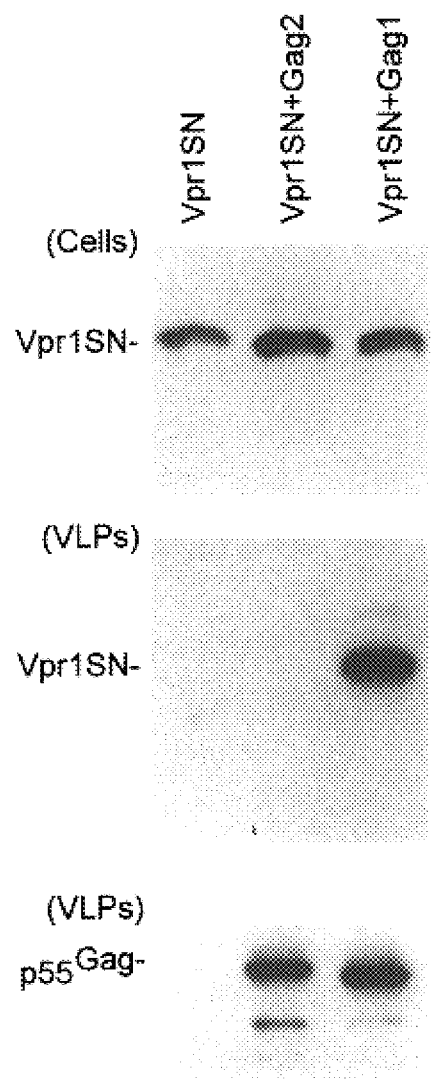
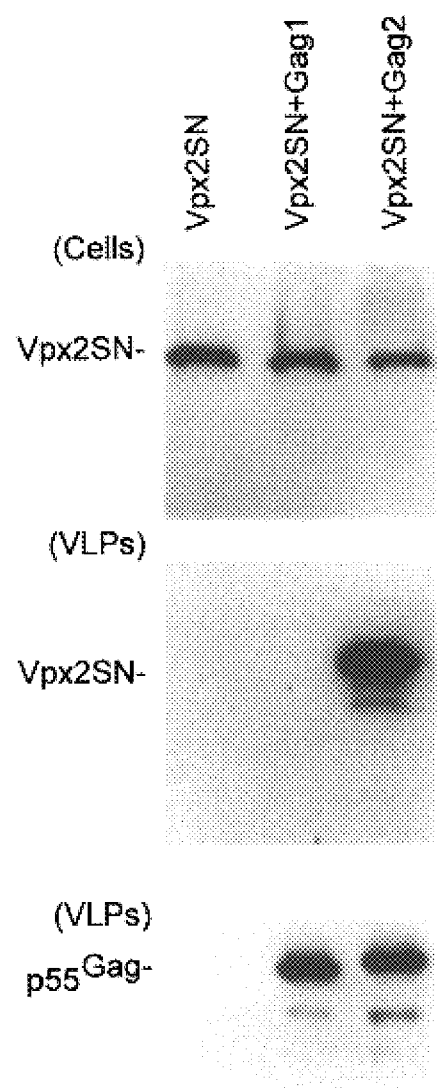
*FIG. 4A*  *FIG. 4B*

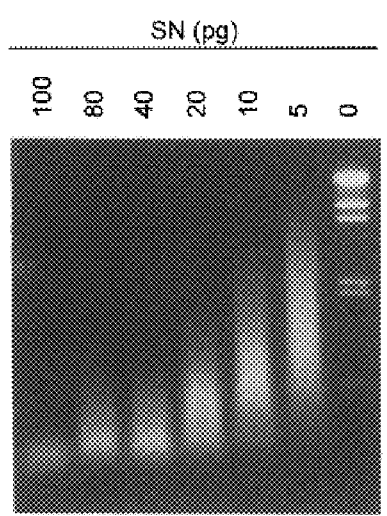 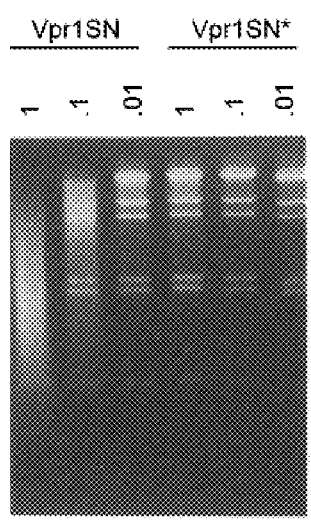 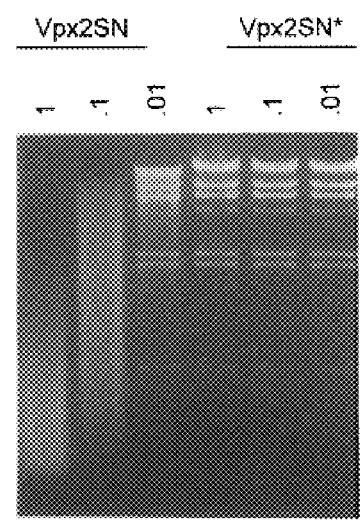
*FIG. 6A*     *FIG. 6B*     *FIG. 6C*

FUSION PROTEIN DELIVERY SYSTEM AND USES THEREOF

RELATED APPLICATION

This patent application is a divisional of patent application Ser. No. 08/947,516 filed Sep. 29, 1997 U.S. Pat. No. 6,001,985, which is a file-wrapper continuation of patent application Ser. No. 08/421,982 filed Apr. 14, 1995 now abandoned, of which both are incorporated herein by reference.

BACKGROUND OF THE INVENTION

1. Field of the Invention

The present invention relates generally to the fields of molecular virology and protein chemistry. More specifically, the present invention relates to the use of Human and Simian Immunodeficiency Virus (HIV/SIV) Vpx and Vpr proteins, or amino acid residues that mediate their packaging, as vehicles for delivery of proteins/peptides to virions or virus-like particles and uses thereof.

2. Description of the Related Art

Unlike simple retroviruses, human and simian immunodeficiency viruses (HIV/SIV) encode proteins in addition to Gag, Pol, and Env that are packaged into virus particles. These include the Vpr protein, present in all primate lentiviral, and the Vpx protein, which is unique to the HIV-2/$SIV_{SM}$/$SIV_{MAC}$ group of viruses. Since Vpr and Vpx are present in infectious virions, they have long been thought to play important roles early in the virus life cycle. Indeed, recent studies of HIV-1 have shown that Vpr has nucleophilic properties and that it facilitates, together with the matrix protein, nuclear transport of the viral preintegration complex in nondividing cells, such as the macrophage. Similarly, Vpx-deficient HIV-2 has been shown to exhibit delayed replication kinetics and to require 2–3 orders of magnitude more virus to produce and maintain a productive infection in peripheral blood mononuclear cells. Thus, both accessory proteins appear to be important for efficient replication and spread of HIV/SIV in primary target cells.

Incorporation of foreign proteins into retrovirus particles has previously been reported by fusion with gag. Using the yeast retrotransposon Ty1 as a retrovirus assembly model, Natsoulis and Boeke tested this approach as a novel means to interfere with viral replication. More recently, the expression of a murine retrovirus capsid-staphylococcal nuclease fusion protein was found to inhibit murine leukemia virus replication in tissue culture cells.

The prior art lacks effective means of delivering or targeting foreign, e.g., toxic proteins to virions. The present invention fulfills this longstanding need and desire in the art.

SUMMARY OF THE INVENTION

Vpr and Vpx packaging is mediated by the Gag precursor and thus must play an important role in HIV assembly processes. The present invention shows that Vpr and Vpx can be used as vehicles to target foreign proteins to HIV/SIV virions. Vpr1 and Vpx2 gene fusions were constructed with bacterial staphylococcal nuclease (SN) and chloramphenicol acetyl transferase (CAT) genes. Unlike Gag or Pol proteins, Vpr and Vpx are dispensable for viral replication in immortalized T-cell lines. Thus, structural alteration of these accessory proteins may be more readily tolerated than similar changes in Gag or Gag/Pol. Fusion proteins containing a Vpx or Vpr moiety should be packaged into HIV particles by expression in trans, since their incorporation should be mediated by the same interactions with Gag that facilitates wild-type Vpr and Vpx protein packaging.

Vpr and Vpx fusion proteins were constructed and their abilities to package into HIV particles were demonstrated. Fusion partners selected for demonstration were: staphylococcal nuclease because of its potential to degrade viral nucleic acid upon packaging and the chloramphenicol acetyl transferase because of its utility as a functional marker. To control for cytotoxicity, an enzymatically inactive nuclease mutant (SN*), derived from SN by site-directed mutagenesis was also used. This SN* mutant differs from wild-type SN by two amino acid substitutions; Glu was changed to Ser (position 43) and Arg was changed to Gly (position 87). SN* folds normally, but has a specific activity that is $10^6$-fold lower than wild-type SN. Using transient expression systems and in trans complementation approaches, fusion protein stability, function and packaging requirements was shown. The present invention shows that Vpr1 and Vpx2 fusion proteins were expressed in mammalian cells and were incorporated into HIV particles even in the presence of wild-type Vpr and/or Vpx proteins. More importantly, however, the present invention shows that virion incorporated Vpr and Vpx fusions remain enzymatically active. Thus, targeting heterologous Vpr and Vpx fusion proteins, including deleterious enzymes, to virions represents a new avenue toward anti-HIV drug discovery.

In one embodiment of the present invention, there is provided a composition of matter, comprising: DNA encoding a viral Vpx protein fused to DNA encoding a virus inhibitory protein.

In another embodiment of the present invention, there is provided a composition of matter, comprising: DNA encoding a viral Vpr protein fused to DNA encoding a virus inhibitory protein.

In yet another embodiment of the present invention, there is provided a method of delivering a virus inhibitory molecule to a target in an animal, comprising the step of administering to said animal an effective amount of the composition of the present invention.

In still yet another embodiment of the present invention, there is provided a pharmaceutical composition, comprising a composition of the present invention and a pharmaceutically acceptable carrier.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1A shows the illustration of the pTM-vpr1 expression plasmid. The HIV-$1_{YU2}$ vpr coding region was amplified by PCR and ligated into pTM1 at the NcoI and BamHI restriction sites.

FIG. 1B shows the illustration of the pTM-vpx2 expression plasmid. The HIV-2$_{ST}$ vpx coding region was amplified by PCR and ligated into pTM1 at the NcoI and BglII/SmaI sites.

FIG. 1C shows the illustration of the fusion junctions of the pTM-vpr1 SN/SN* expression plasmids. SmaI/XhoI DNA fragments containing SN and SN* were ligated into HpaI/XhoI cut pTM-vpr1. Blunt-end ligation at HpaI and SmaI sites changes the vpr translational stop codon (TAA) to Trp and substituted the C terminal Ser with a Cys residue.

FIG. 1D shows the illustration of the fusion junctions of the pTM-vpx2SN/SN* expression plasmids. BamHI/XhoI DNA fragments containing SN and SN* were ligated into BamHI/XhoI cut pTM-vpx2. In the construction of these plasmids, the Vpx C terminal Arg codon was changed to a Val codon and a Ser residue was introduced in place of the Vpx translational stop codon (TAA). Fusion of vpx and SN/SN* at the BamHI sites left a short amino acid sequence of the pTM1 polylinker (double underlined) between the two coding regions.

FIG. 2A shows the pTM1, pTM-vpr1, pTM-vpr1SN and pTM-vpr1SN* were transfected into HeLa cells one hour after infection with rVT7 (MOI=10). Twenty-four hours later cell lysates were prepared and examined by immunoblot analysis. Replica blots were probed with anti-Vpr1 (left) and anti-SN (right) antibodies.

FIG. 2B shows that replica blots, prepared from rVT7 infected HeLa cells transfected with pTM1, pTM-vpx2, pTM-vpx2SN and pTM-vpx2SN*, were probed with anti-Vpx2 (left) and anti-SN (right) antibodies. Bound antibodies were detected by ECL (Amersham) methods as described by the manufacturer.

FIG. 3A transfection of T7 expressing (rVT7 infected) HeLa cells with pTM-vpr1, pTM-vpr1SN, and pTM-vpr1SN* alone and in combination with pTM-gag1. pTM1 was also transfected for control. Culture supernatant were collected twenty-four hours after transfection, clarified by centrifugation (1000×g, 10 min.) and ultracentrifuged (125,000×g, 2 hrs.) over cushions of 20% sucrose. Pellets (VLPs, middle and bottom panels) and cells (top panel) were solubilized in loading buffer and examined by immunoblot analysis using anti-Vpr1 (top and middle) and anti-Gag (bottom) antibodies as probes.

FIGS. 4A and 4B show that virus-specific signals mediate incorporation of Vpr- and Vpx-SN into VLPs.

FIG. 4A shows that HIV-1 Gag mediates packaging of Vpr1SN. rVT7 infected (T7 expressing) HeLa cells were transfected with pTM-vpr1SN alone and in combination with pTM-gag2 and pTM-gag1. Pellets (VLPs, middle and bottom panels) and cells (top panel) were prepared 24 hours after transfection and examined by immunoblot analysis using anti-Vpr1 (top and middle) and anti-Gag (bottom) antibodies for probes.

FIG. 4B shows that HIV-2 Gag mediates packaging of Vpx2SN. T7 expressing HeLa cells were transfected with pTM-vpx2SN alone and in combination with pTM-gag1 and pTM-gag2. Pellets (VLPs, middle and bottom panels) and cells (top panel) were prepared 24 hours after transfection and examined by immunoblot analysis using anti-Vpx2 (top and middle) and anti-Gag (bottom) antibodies for probes.

FIG. 5A shows transfection of T7 expressing HeLa cells with different amounts of pTM-vpr1 (2.5, 5 and 10 ug) and pTM-vpr1SN (2.5, 5 and 10 ug), either individually or together in combination with pTM-gag1 (10 ug).

FIG. 5B shows that HeLa cells were transfected with different amounts of pTM-vpx2 (2.5, 5 and 10 ug) and pTM-vpx2SN (2.5, 5 and 10 ug), either individually or together with pTM-gag2 (10 ug). Twenty hours after transfection, particles were concentrated by ultracentrifugation through sucrose cushions and analyzed by immunoblotting using anti-Vpr1 (A) or anti-Vpx2 (B) antibodies.

FIGS. 6A–C show the nuclease activity of VLP-associated Vpr1SN and Vpx2SN proteins. Virus-like particles were concentrated from culture supernatants of T7 expressing HeLa cells cotransfected with pTM-gag1/pTM-vpr1SN, pTM-gag1/pTM-vpr1SN*, pTM-gag2/pTM-vpx2SN and pTM-gag2/pTM-vpx2SN* by ultracentrifugation (125,000×g, 2 hrs.) through 20% cushions of sucrose. Pellets containing Vpr1-SN and SN* (B) and Vpx2-SN and SN* (C) were resuspended in PBS. Tenfold dilutions were made in nuclease reaction cocktail buffer (100 mM Tris-HCl pH 8.8, 10 mM CaCl$_2$, 0.1% NP40) and boiled for 1 minute. 5 ul of each dilution was added to 14 ul of reaction cocktail buffer containing 500 ng of lambda phage DNA (HindIII fragments) and incubated at 37° C. for 2 hours. Reaction products were electrophoresed on 0.8% agarose gels and DNA was visualized by ethidium bromide staining. Standards (A) were prepared by dilution of purified staphylococcal nuclease (provided by A. Mildvan) into cocktail buffer and assayed.

FIG. 7A shows the construction of the pLR2P-vpx2SN/SN* expression plasmids. To facilitate efficient expression of HIV genes, the HIV-2 LTR and RRE were engineered into the polylinker of pTZ19U, generating pLR2P. The organization of these elements within the pTZ19U polylinker is illustrated. NcoI/XhoI vpx2SN and vpx2SN* (vpxSN/SN*) containing DNA fragments were ligated into pLR2P, generating pLR2P-vpx2SN and pLR2P-vpx2SN* (pLR2P-vpxSN/SN*).

FIG. 7B shows the association of Vpx2SN with HIV-2 virions. Monolayer cultures of HLtat cells were transfected with HIV-2$_{ST}$ proviral DNA (pSXB1) and cotransfected with pSXB1/pTM-vpx2SN and pSXB1/pTM-vpx2SN*. Extracellular virus was concentrated from culture supernatants forty-eight hours after transfection by ultracentrifugation (125,000×g, 2 hrs.) through cushions of 20% sucrose. Duplicate Western blots of viral pellets were prepared and probed independently with anti-Vpx2 (left) anti-SN (middle) and anti-Gag (right) antibodies.

FIG. 7C shows a sucrose gradient analysis. Pellets of supernatant-virus prepared from pSXB1/pTM-vpx2SN cotransfected HLtat cells were resuspended in PBS, layered over a 20–60% linear gradient of sucrose and centrifuged for 18 hours at 125,000×g. Fractions (0.5 ml) were collected from the bottom of the tube, diluted 1:3 in PBS, reprecipitated and solubilized in electrophoresis buffer for immunoblot analysis. Replica blots were probed with anti-SN (top) and anti-Gag (bottom) antibodies. Fraction 1 represents the first collection from the bottom of the gradient and fraction 19 represents the last collection. Only alternate fractions are shown, except at the peak of protein detection.

FIG. 7D shows the incorporation of Vpx2SN into HIV-$2_{7312A}$ Vpr and Vpx competent virus. Virus concentrated from supernatants of HLtat cells transfected with HIV-$2_{7312A}$ proviral DNA (pJK) or cotransfected with pJK/pLR2P-vpx2SN or pJK/pLR2P-vpx2SN* was prepared for immunoblot analysis as described above. Included for control were virions derived by pSXB1/pLR2P-vpx2SN* cotransfection. Duplicate blots were probed with anti-Vpx (left) and anti-Gag (right) antibodies.

FIG. 10A shows an illustration of the fusion junctions of the pLR2P-vpr1CAT and pLR2P-vpx2CAT expression plasmids. PCR amplified BamHI/XhoI DNA fragments containing CAT were ligated into BgIII/XhoI cut pLR2P-vpr1SN and pLR2P-vpx2SAN, replacing SN (see FIG. 1). This construction introduced two additional amino acid residues (Asp and Leu, above blackened bar) between the vpr1/vpx2CAT coding regions.

FIG. 10B shows the incorporation of Vpr1CAT into HIV-1 virions. Virus produced from HLtat cells transfected with pNL4-3 (HIV-1) and pNL4-3R$^-$ (HIV-1-R$^-$), or cotransfected with pNL4-3/pLR2P-vpr1CAT and pNL4-3R$^-$/pLR2P-vpr1CAT was prepared as described above and examined by immunoblot analysis. Replica blots were probed with anti-Vpr1 (left) and anti-Gag (right) antibodies.

FIG. 11A shows that HIV-2 virions collected from the culture supernatant of HILtat cells cotransfected with pSXB1 and pLR2P-vpx2 were sedimented in linear gradients of 20–60% sucrose. 0.7 ml fractions were collected and analyzed by immunoblot analysis using Gag monoclonal antibodies as a probe.

FIG. 11B shows CAT enzyme activity was determined in each fraction by standard methods. The positions of non-acetylated [$^{14}$C]chloramphenicol (Cm) and acetylated chloramphenicol (Ac-Cm) are indicated.

FIG. 11C shows HIV-1 virions derived from HLtat cells cotransfected with pSG3 and pLR2P-vpr1SN and cultured in the presence of L-689,502 were sedimented in linear gradients of 20–60% sucrose. Fractions were collected and analyzed for virus content by immunoblot analysis using Gag monoclonal antibodies.

FIG. 11D shows that SN activity was determined in each fraction as described in FIG. 6.

DETAILED DESCRIPTION OF THE INVENTION

Figure 1A:
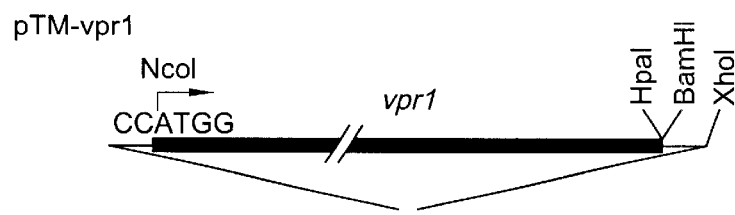
FIGS. 1A–D show the construction of vpr1, vpr1SN/SN*, vpx2 and vpx2SN/SN* expression plasmids.

As used herein, the term "fusion protein" refers to either the entire native protein amino acid sequence of Vpx (of any HIV-2 and SIV) and Vpr (of any HIV-1 and SIV) or any subfraction of their sequences that have been joined through recombinant DNA technology and are capable of association with either native HIV/SIV virions or virus like particles.

As used herein, the term "virion" refers to HIV-1, HIV-2 and SIV virus particles.

As used herein, the term "virus-like particle" refers to any composition of HIV-1, HIV-2 and SIV proteins other than which exists naturally in naturally infected individuals or monkey species that are capable of assembly and release from either natural or immortalized cells that express these proteins.

As used herein, the term "transfect" refers to the introduction of nucleic acids (either DNA or RNA) into eukaryotic or prokaryotic cells or organisms.

As used herein, the term "virus-inhibitory protein" refers to any sequence of amino acids that have been fused with Vpx or Vpr sequences that may alter in any way the ability of HIV-1, HIV-2 or SIV viruses to multiply and spread in either individual cells (prokaryotic and eukaryotic) or in higher organisms. Such inhibitory molecules may include: HIV/SIV proteins or sequences, including those that may possess enzymatic activity (examples may include the HIV/SIV protease, integrase, reverse transcriptase, Vif, Nef and Gag proteins) HIV/SIV proteins or proteins/peptide sequences that have been modified by genetic engineering technologies in order to alter in any way their normal function or enzymatic activity and/or specificity (examples may include mutations of the HIV/SIV protease, integrase, reverse transcriptase, Vif, Nef and Gag proteins), or any other non viral protein that, when expressed as a fusion protein with Vpx or Vpr, alter virus multiplication and spread in vitro or in vivo.

In the present invention, the HIV Vpr and Vpx proteins were packaged into virions through virus type-specific interactions with the Gag polyprotein precursor. HIV-1 Vpr (Vpr1) and HIV-2 Vpx (Vpx2) are utilized to target foreign proteins to the HIV particle as their open reading frames were fused in-frame with genes encoding the bacterial staphylococcal nuclease (SN), an enzymatically inactive mutant of SN (SN*), and the chloramphenicol acetyl transferase (CAT). Transient expression in a T7-based vaccinia virus system demonstrated the synthesis of appropriately sized Vpr1SN/SN* and Vpx2SN/SN* fusion proteins which, when co-expressed with their cognate p55$^{Gag}$ protein, were efficiently incorporated into virus-like particles (VLPs). Packaging of the fusion proteins was dependent on virus type-specific determinants, as previously seen with wild-type Vpr and Vpx proteins. Particle associated Vpr1SN and Vpx2SN fusion proteins were enzymatically active as determined by in vitro digestion of lambda phage DNA. To demonstrate that functional Vpr1 and Vpx2 fusion proteins were targeted to HIV particles, the gene-fusions were cloned into an HIV-2 LTR/RRE regulated expression vector and co-transfected with wild-type HIV-1 and HIV-2 proviruses. Western blot analysis of sucrose gradient purified virions revealed that both Vpr1 and Vpx2 fusion proteins were efficiently packaged regardless of whether SN, SN* or CAT were used as C terminal fusion partners. Moreover, the fusion proteins remained enzymatically active and were packaged in the presence of wild-type Vpr and Vpx proteins. Interestingly, virions also contained smaller sized proteins that reacted with antibodies specific for the accessory proteins as well as SN and CAT fusion partners. Since similar proteins were absent from Gag-derived VLPs as well as in virions propagated in the presence of an HIV protease inhibitor, they must represent cleavage products produced by the viral protease. Taken together, these results demonstrate that Vpr and Vpx can be used to target functional proteins, including potentially deleterious enzymes, to the HIV/SIV particle. These properties are useful for the development of novel antiviral strategies.

The following examples are given for the purpose of illustrating various embodiments of the invention and are not meant to limit the present invention in any fashion.

EXAMPLE 1

Cells and Viruses

HeLa, HeLa-tat (HLtat) and CV-1 cells were maintained in Dulbecco's Modified Eagle's Medium supplemented with 10% fetal bovine serum (FBS). HLtat cells constitutively express the first exon of HIV-1 tat and were provided by Drs. B. Felber and G. Pavlakis. A recombinant vaccinia virus (rVT7) containing the bacteriophage T7 RNA polymerase gene was used to facilitate expression of viral genes placed under the control of a T7 promoter. Stocks of rVT7 were prepared and titrated in CV-1 cells as described previously by Wu, et al., J. Virol. 66:7104–7112 (1992). HIV-1$_{YU2}$, HIV-1 pNL 4-3-R$^-$ and pNL 4-3, HIV-1$_{HXB2D}$, HIV-2$_{ST}$, and HIV-2$_{7312A}$ proviral clones were used for the construction of recombinant expression plasmids and the generation of transfection derived viruses.

EXAMPLE 2

Antibodies

To generate HIV-1 Vpr specific antibodies, the HIV-1$_{YU-2}$ vpr open reading frame was amplified by polymerase chain reaction (PCR) using primers (sense: 5'GCCACCTTTGTCGACTGTTAAAAAACT-3' SEQ ID NO.1 and anti-sense: 5'-GTCCTAGGCAAGCTTCCTGGA TGC-3' SEQ ID NO.2) containing SalI and HindIII sites and ligated into the prokaryotic expression vector, pGEX, generating pGEX-vpr1. This construct allowed expression of Vpr1 as a C terminal fusion protein and glutathione S-transferase (gst), thus allowing protein purification using affinity chromatography. E. coli (DH5a) were transformed with pGEX-vpr1 and protein expression was induced with isopropyl β-D thiogalactopyranoside (IPTG). Expression of the gst-Vpr1 fusion protein was confirmed by SDS-PAGE. Soluble gst-Vpr1 protein was purified and Vpr1 was released by thrombin cleavage using previously described procedures of Smith, et al., Gene 67:31–40 (1988). New Zealand White rabbits were immunized with 0.4 mg of purified Vpr1 protein emulsified 1:1 in Freunds complete adjuvant, boosted three times at two week intervals with 0.25 mg of Vpr1 mixed 1:1 in Freunds' incomplete adjuvant and bled eight and ten weeks after the first immunization to collect antisera. Additional antibodies used included monoclonal antibodies to HIV-1 Gag (ACT1, and HIV-2 Gag (6D2.6), polyclonal rabbit antibodies raised against the HIV-2 Vpx protein and anti-SN antiserum raised against purified bacterially expressed SN protein.

EXAMPLE 3

Construction of T7-based Expression Plasmids

A DNA fragment encompassing $^{HIV-1}$HXB2D$^{gag}$ (nucleotides 335–1837) was amplified by PCR using primers (sense: 5'-AAGGAGAGCCATGGGTGCGAGAGCG-' SEQ ID NO:3 and anti-sense: 5'GG GGATCCCTTTATTGTGACGAGGGG-3' SEQ ID NO:4) containing NcoI and BamHI restriction sites, respectively (underlined). The PCR product was digested with NcoI and BamHI, purified and ligated into the polylinker of the pTM1 vector, generating pTM-gag1. Similarly, a DNA fragment containing the gag coding region of HIV-2$_{ST}$ (nucleotides 547–2113) was amplified by PCR using sense and anti-sense primers 5'-ATTGTGGGCCATGGGCGCGAGAAAC-3' SEQ ID NO:6 and 5'-GGGGGGCCCCTACTGGTCTTTTC C-3', respectively. The reaction product was cut with NcoI and SmaI (underlined), purified and ligated into the polylinker of pTM1, generating pTM-gag2.

Figure 1B:
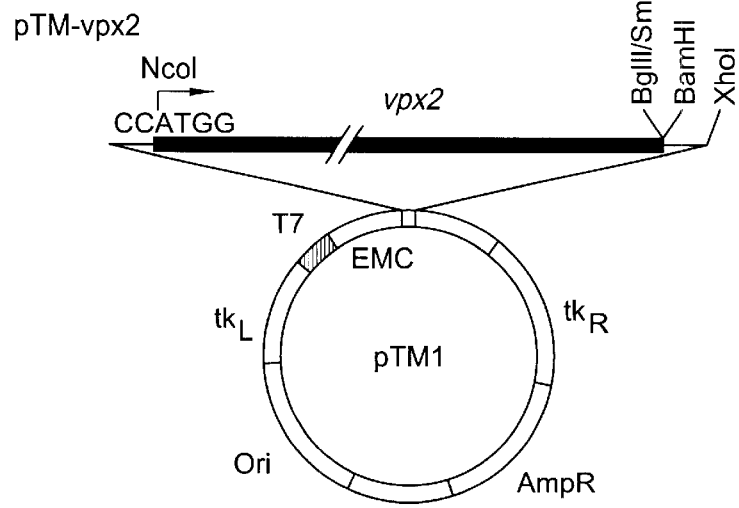
Figure 1C:
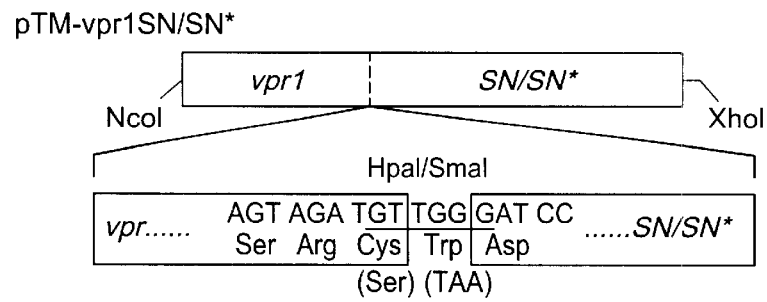

For expression of Vpr1 under the control of the T7 promoter, a DNA fragment containing the HIV-1$_{YU2}$ vpr coding region (nucleotides 5107–5400) was amplified by PCR using primers (sense: 5'-GAAGATCTA CCATGGAAGCCCCAGAAGA-' SEQ ID NO. 7 and anti-sense: 5'-CGCGGATCCGTTAACATCTACTGGCTCCATT TCTTGCTC-3' SEQ ID NO:8) containing NcoI and HpaI/BamHI sites, respectively (underlined). The reaction product was cut with NcoI and BamHI and ligated into pTM1, generating a pTM-vpr1 (FIG. 12A). In order to fuse SN and SN* in-frame with vpr1, their coding regions were excised from pGN1561.1 and pGN1709.3, respectively and through a series of subcloning steps, ligated into the SmaI/XhoI sites of pTM-vpr1, generating pTM-vpr1Sn and pTM-vpr1Sn*. This approach changed the translational stop codon of Vpr1 to a Trp codon and the C terminal Ser residue to a Cys. The resulting junctions between vpr1 and SN/SN* are depicted in FIG. 1C.

Figure 1D:
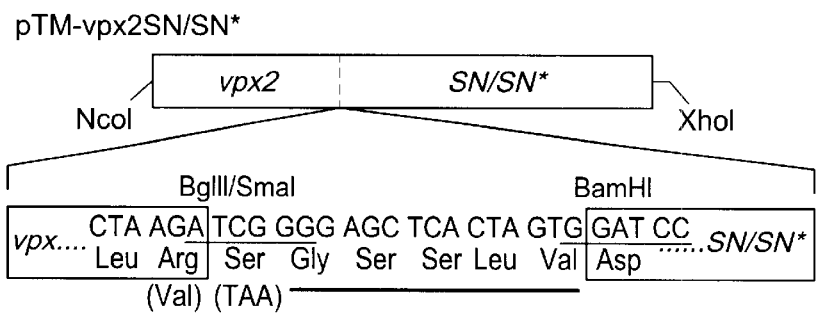

For expression of Vpx2 under T7 control, a DNA fragment containing the HIV-2$_{ST}$ vpx coding sequence (nucleotides 5343–5691) was amplified by PCR using primers (sense: 5'GTGCAACACCATGGCAGGCCCCAGA-3' SEQ ID NO.9 and anti-sense: 5'-TGCACTGCAGGA AGATCTTAGACCTGGAGGGGGAGGAGG-3' SEQ ID NO. 10) containing NcoI and BglII sites, respectively (underlined). After cleave with BglII and Klenow fill-in, the PCR product was cleaved with NcoI, purified and ligated into the NcoI and SmaI sites of pTM1, generating pTM-vpx2 (FIG. 1B). To construct in-frame fusions with vpx2, BamHI/XhoI, SN- and SN*-containing DNA fragments were excised from pTM-vpr1SN and pTM-vpr1SN* and ligated into pTM-vpx2, generating pTM-vpx2SN and pTM-vpx2SN*, respectively. This approach introduced one amino acid substitution at the C terminus of Vpx (Val to Arg), changed the translational stop codon of vpx to Ser and left five amino acids residues of the pTM1 plasmid polylinker. The resulting junctions between vpx2 and SN/SN* are depicted in FIG. 1D.

EXAMPLE 4
Construction of HIV LTR-based Expression Plasmids

Figure 7A:
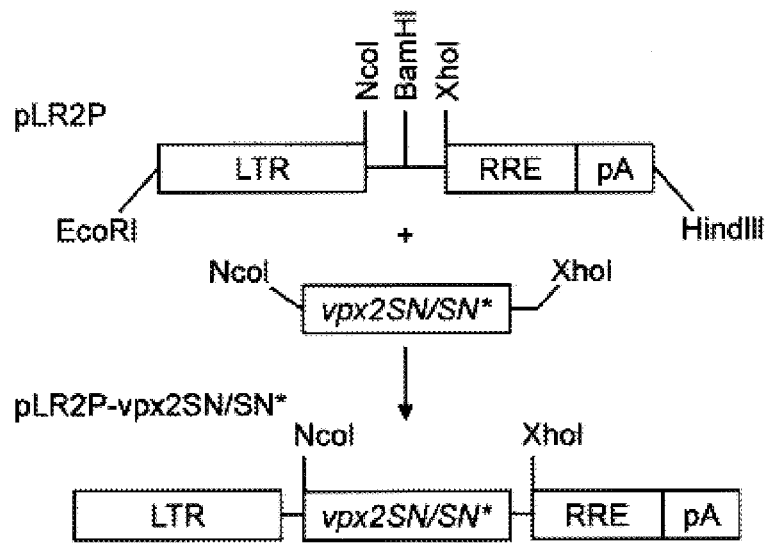
FIGS. 7A–D show the incorporation of Vpx2SN into HIV-2 by trans complementation.
Figure 9:
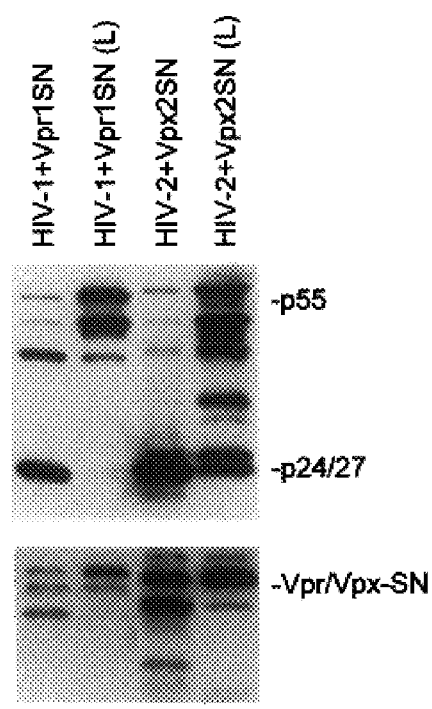
FIG. 9 shows the inhibition of Vpr1/Vpx2-SN processing by an HIV protease inhibitor. HIV-1 (pSG3) and HIV-2 (pSXB1) proviral DNAs were cotransfected separately into replica cultures of HLtat cells with pLR2P-vpr1SN and pLR2P-vpx2SN, respectively. One culture of each transfection contained medium supplemented with 1 uM of the HIV protease inhibitor L-699-502. Virions were concentrated from culture supernatants by ultracentrifugation through cushions of 20% sucrose and examined by immunoblot analysis using anti-Gag (FIG. 9A) and anti-SN (FIG. 9B) antibodies.

For efficient expression of Vpr and Vpx fusion proteins in the presence of HIV, a eukaryotic expression vector (termed pLR2P) was constructed which contains both an HIV-2 LTR (HIV-$2_{ST}$, coordinates -544 to 466) and an HIV-2 RRE (HIV-$2_{ROD}$, coordinates 7320 to 7972) element (FIG. 7A). These HIV-2 LTR and RRE elements were chosen because they respond to both HIV-1 and HIV-2 Tat and Rev proteins. The vpr1, vpr1SN, vpx2 and vpx2SN coding regions were excised from their respective pTM expression plasmids (see FIG. 1) with NcoI and XhoI restriction enzymes and ligated into pLR2P, generating pLR2P-vpr1, pLR2P-vpr1SN, pLR2P-vpx2 and pLR2P-vpx2SN, respectively (FIG. 7A). For construction and expression of vpr- and vpx-CAT gene fusions, the SN containing regions (BamHI/XhoI fragments) of pLR2P-vpr1Sn and pLR2P-vpx2SN were removed and substituted with a PCR amplified BglII/XhoI DNA fragment containing CAT, generating pLR2P-vpr1CAT and pLR2P-vpx2CAT, respectively (FIG. 9A).

EXAMPLE 5
Transfections

Transfections of proviral clones were performed in HLtat cells using calcium phosphate DNA precipitation methods as described by the manufacturer (Strategene). T7-based (pTM1) expression constructs were transfected using Lipofectin (BioRad) into rVT7 infected HeLa cells as described previously by Wu, et al., *J. Virol.* 68:61 61–6169 (1994). These methods were those recommended by the manufacturer of-the Lipofectin reagent.

EXAMPLE 6
Western Immunoblot Analysis

Virions and virus-like particles (VLPs) were concentrated from the supernatants of transfected or infected cells by ultracentrifugation through 20% cushions of sucrose (125,000×g, 2 hrs., 4° C.). Pellets and infected/transfected cells were solubilized in loading buffer [62.5 mM Tris-HCl (pH 6.8) 0.2% sodium dodecyl sulfate (SDS), 5% 2-mercaptoethanol, 10% glycerol], boiled and separated on 12.5% polyacrylamide gels containing SDS. Following electrophoresis, proteins were transferred to nitrocellulose (0.2 μm; Schleicher & Schuell) by electroblotting, incubated for one hour at room temperature in blocking buffer (5% nonfat dry milk in phosphate buffered saline [PBS]) and then for two hours with the appropriate antibodies diluted in blocking buffer. Protein bound antibodies were detected with HRP-conjugated specific secondary antibodies using ECL methods according to the manufacturer's instructions (Amersham).

EXAMPLE 7
SN Nuclease Activity Assay

Cells and viral pellets were resuspended in nuclease lysis buffer (40 mM Tris-HCl, pH 6.8, 100 mM NaCl, 0.1% SDS, 1% Triton X-100) and clarified by low speed centrifugation (1000×g, 10 min.). Tenfold dilutions were made in nuclease reaction cocktail buffer (100 mM Tris-HCl, pH 8.8, 10 mM $CaCl_2$, 0.1% NP40) and boiled for 1 minute. 5 μl of each dilution was added to 14 μl of reaction cocktail buffer containing 500 ng of lambda phage DNA (HindIII fragments) and incubated at 37° C. for 2 hours. Reaction products were electrophoresed on 0.8% agarose gels and DNA was visualized by ethidium bromide staining.

Figure 2A:
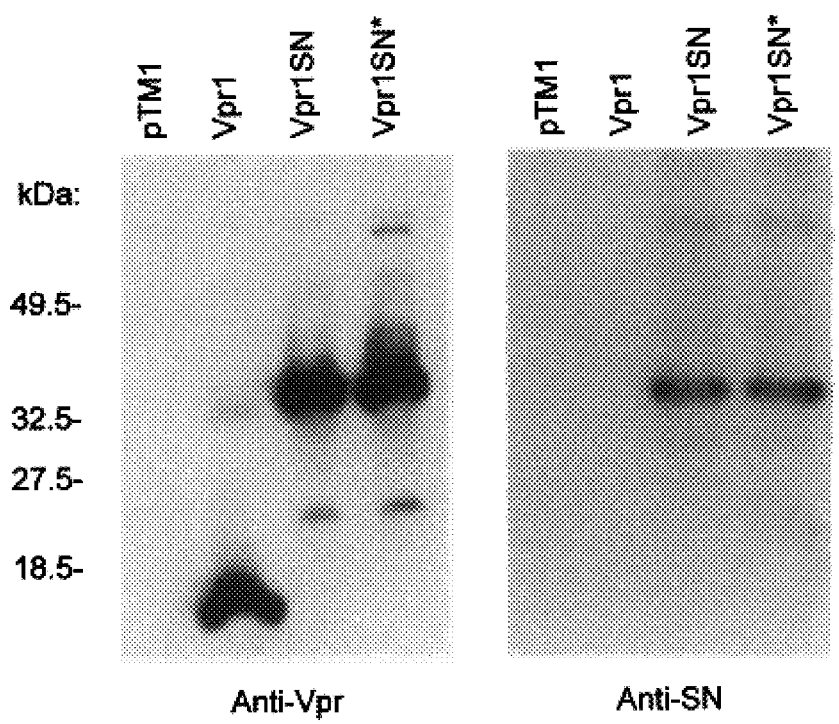
FIGS. 2A and 2B show the expression of Vpr1- and VPX2-SN and SN* fusion proteins in mammalian cells.
Figure 2B:
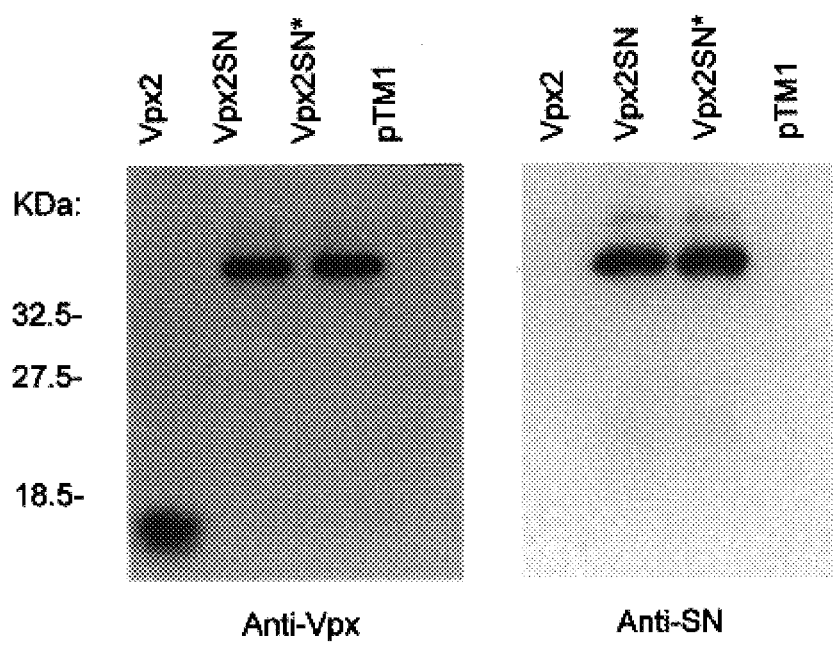

EXAMPLE 8
Expression of Vpr1- and Vpx2-SN and SN* Fusion Proteins in Mammalian Cells Expression of Vpr1- and Vpx2-SN/SN* fusion proteins in mammalian cells was assessed using the recombinant vaccinia virus-T7 system (rVT7). HeLa cells were grown to 75–80% confluency and transfected with the recombinant plasmids pTM-vpr, pTM-vpx, pTM-vpr1SN/SN*, and pTM-vpx2SN/SN* (FIG. 1). Twenty-four hours after transfection, cells were washed twice with PBS and lysed. Soluble proteins were separated by SDS-PAGE and subjected to immunoblot blot analysis. The results are shown in FIG. 2. Transfection of pTM-vpr1SN and pTM-vpr1SN* resulted in the expression of a 34 kDa fusion protein that was detectable using both anti-Vpr and anti-SN antibodies (A). Similarly, transfection of pTM-vpx2SN and pTM-vpx2SN* resulted in the expression of a 35 kDa fusion protein which was detected using anti-Vpx and anti-SN antibodies (B). Both fusion proteins were found to migrate slightly slower than expected, based on the combined molecular weights of Vpr1 (14.5 kDa) and SN (16 kDa) and Vpx2 (15 kDa) and SN, respectively. Transfection of pTM-vpr1 and pTM-vpx2 alone yielded appropriately sized wild-type Vpr and Vpx proteins. Anti-Vpr, anti-Vpx and anti-SN antibodies were not reactive with lysates of pTM1 transfected cells included as controls. Thus, both SN and SN* fusion proteins can be expressed in mammalian cells.

EXAMPLE 9
Incorporation of Vpr1- and Vpr2-SN/SN* fusion proteins into Virus-like Particles In vaccinia and baculovirus systems, the expression of HIV Gag is sufficient for assembly and extracellular release of VLPs. Vpr1 and Vpx2 can be efficiently incorporated into Gag particles without the expression of other viral gene products. To demonstrate that the Vpr1 and Vpx2 fusion proteins could be packaged into VLPs, recombinant plasmids were coexpressed with HIV-1 and HIV-2 Gag proteins in the rVT7 system. pTM-vpr1, pTM-vpr1SN and pTM-vpr1SN* were transfected into HeLa cells alone and in combination with the HIV-1 Gag expression plasmid, pTM-gag1. Twenty-four hours after transfection, cell and VLP extracts were prepared and analyzed by immunoblot analysis (FIG. 3A). Anti-Vpr antibody detected Vpr1, Vpr1SN and Vpr1SN* in cell lysates (top panel) and in pelleted VLPs derived by coexpression with pTM-gag1 (middle panel). In the absence of HIV-lGag expression, Vpr1 and Vpr1SN were not detected in pellets of culture supernatants (middle panel). As expected VLPs also contained p55 Gag (bottom panel). Thus, Vpr1SN/SN* fusion proteins were successfully packaged into VLPs.

To demonstrate that Vpx2SN was similarly capable of packaging into HIV-2 VLPs, pTM-vpx2, pTM-vpx2SN and pTM-vpx2SN* were transfected into HeLa cells alone and in combination with the HIV-2 Gag expression plasmid, pTM-gag2. Western blots were prepared with lysates of cells and VLPs concentrated from culture supernatants by ultracentrifugation (FIG. 3B). Anti-Vpx antibody detected Vpx2, Vpx2SN and Vpx2SN* in cell lysates (top panel) and in VLPs derived by coexpression with pTM-gag2 (middle panel). Anti-Gag antibody detected p55 Gag in VLP pellets (bottom panel). Comparison of the relative protein signal intensities suggested that the Vpr1- and Vpx2-SN and SN* fusion proteins were packaged into VLPs in amounts similar to wild-type Vpr1 and Vpx2 proteins. Sucrose gradient analysis of VLPs containing Vpr1SN and Vpx2SN demonstrated co-sedimentation of these fusion proteins with VLPs (data not shown).

The Gag C terminal region is required for incorporation of Vpr1 and Vpx2 into virions. However, packaging was found to be virus type-specific, that is, when expressed in trans, Vpx2 was only efficiently incorporated into HIV-2 virions and HIV-2 VLPs. Similarly, HIV-1 Vpr required interaction with the HIV-1 Gag precursor for incorporation into HIV-1 VLPs. To show that the association of Vpr1SN and Vpx2SN with VLPs was not mediated by the SN moiety, but was due to the Vpr and Vpx specific packaging signals, pTM-vpr1Sn and pTM-vpx2SN were cotransfected individually with either pTM-gag1 or pTM-gag2. For control, pTM-vpr1 and pTM-vpx2 were also transfected alone. Twenty-four hours later, lysates of cells and pelleted VLPs were examined by immunoblotting (FIG. 4). While Vpr1SN was expressed in all cells (FIG. 4A, top panel), it was only associated with VLPs derived from cells transfected with pTM-gag1. Similarly, Vpx2SN was detected in all pTM-vpx2 transfected cells (FIG. 4B, top panel), but was only associated with VLPs derived by cotransfection with pTM-gag2 (FIG. 4B, middle panel). HIV-1 and HIV-2 Gag monoclonal antibodies confirmed the presence of Gag precursor protein in each VLP pellet (FIG. 4B, bottom panels). Thus, incorporation of Vpr1SN and Vpx2SN into VLPs requires interaction of the cognate Gag precursor protein, just like native Vpr1 and Vpx2.

Figure 3A:
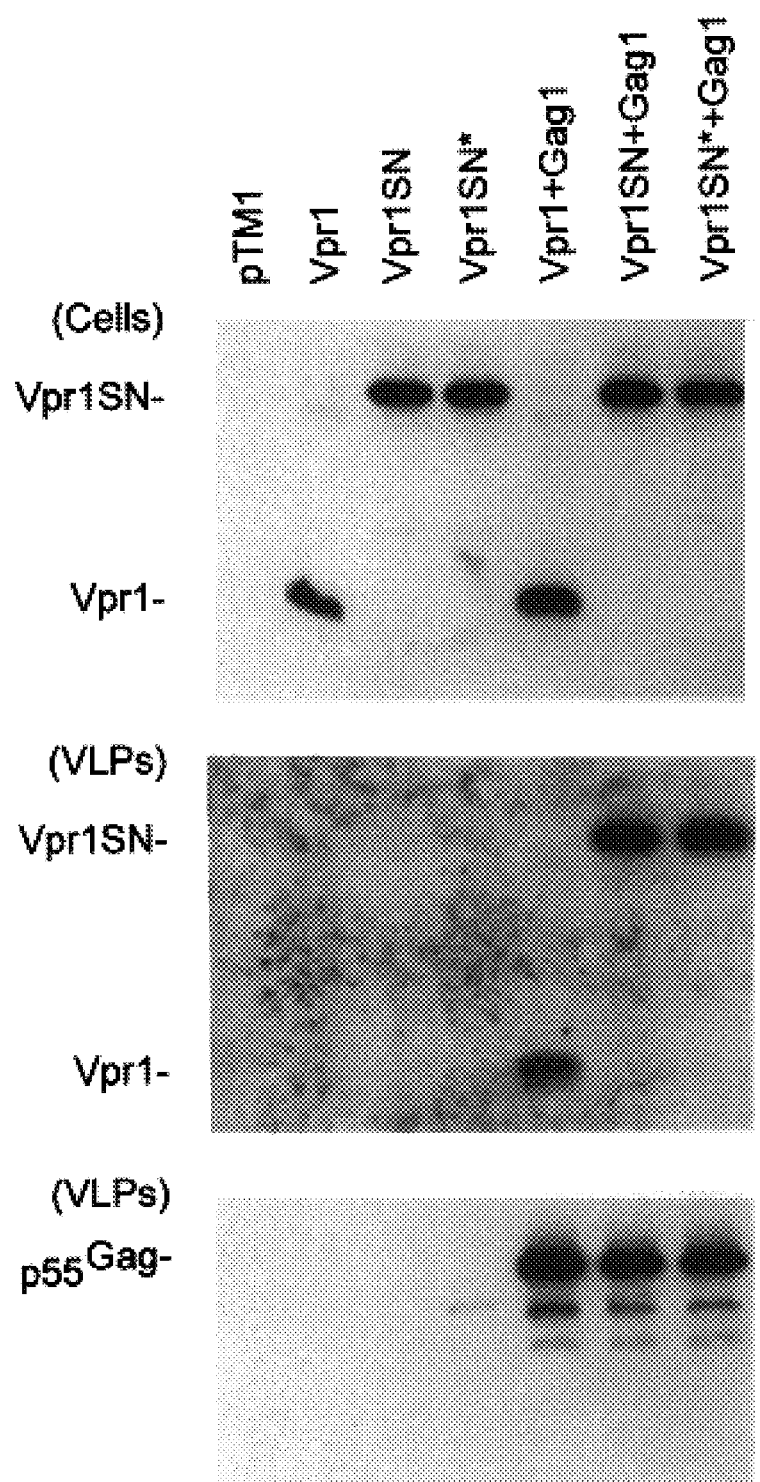
FIG. 3A shows the incorporation of Vpr1- and Vpx2-SN and SN* fusion proteins into virus-like particles (VLP).
Figure 3B:
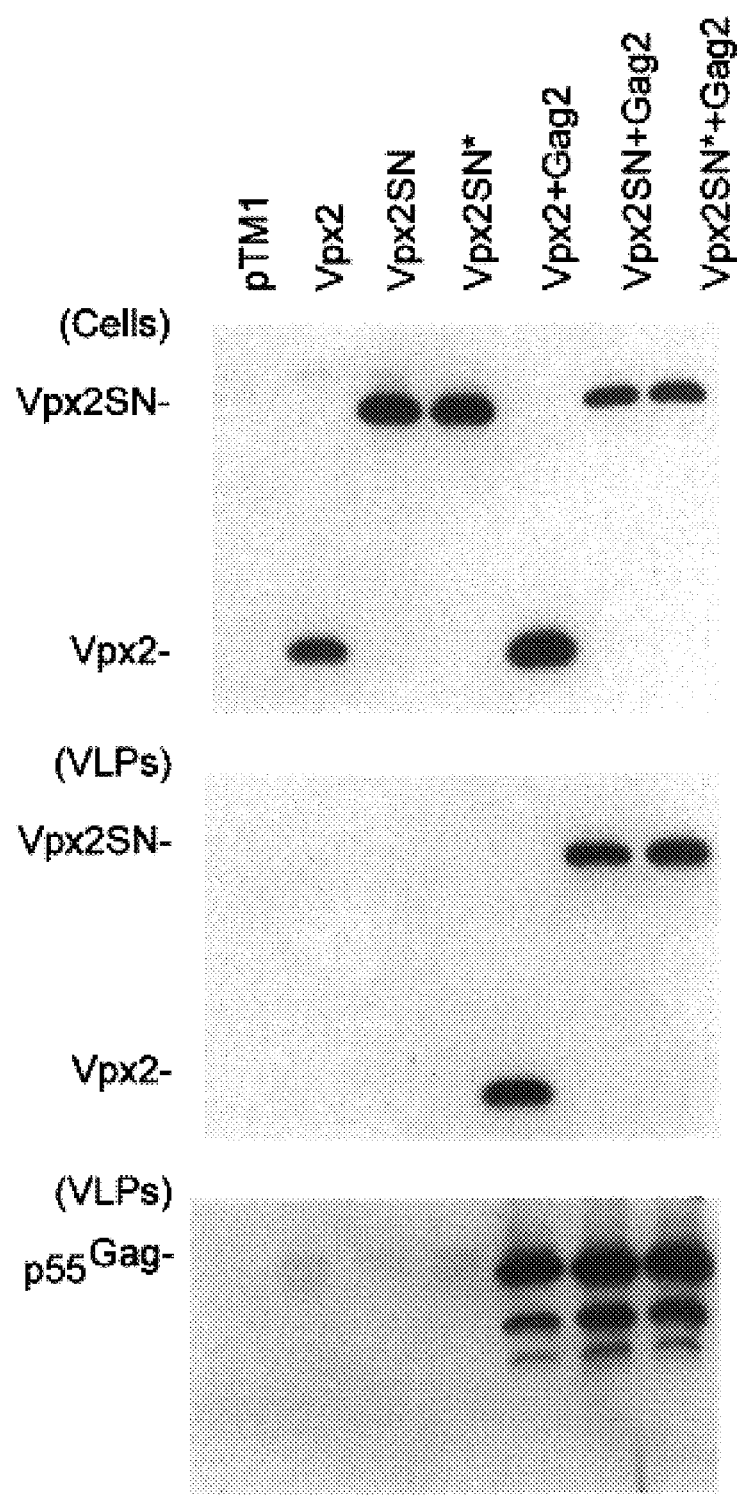
FIG. 3B transfection of T7 expressing HeLa cells pTM-vpx2, pTM-vpx2SN and pTM-vpx2SN* alone and in combination with pTM-gag2. Pellets (VLPs, middle and bottom panels) and cells (top panel) were lysed, proteins were separated by SDS-PAGE and electroblotted blotted to nitrocellulose as described above. Replica blots were probed with anti-Vpx2 (top and middle panels) and anti-Gag (bottom panel) antibodies. Bound antibodies were detected using ECL methods.
Figure 5A:
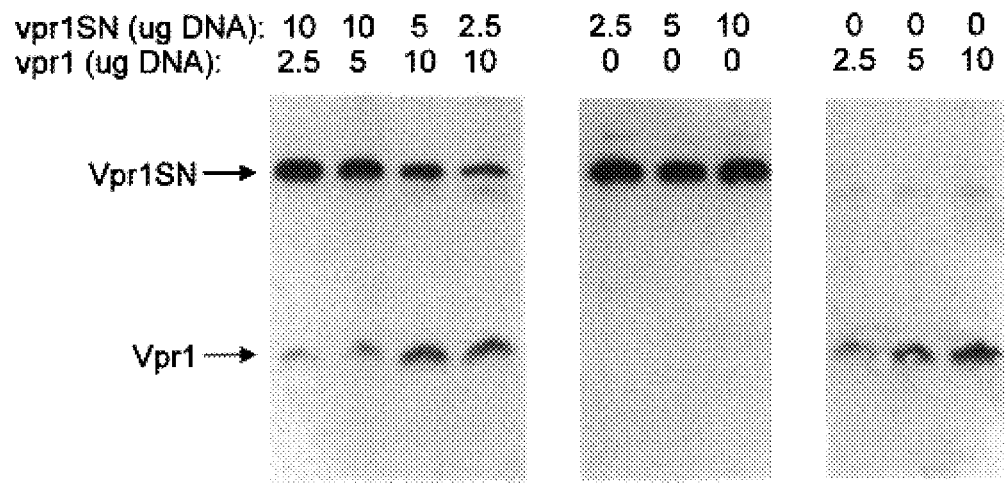
FIGS. 5A and 5B show a competition analysis of Vpr1SN and Vpx2SN for incorporation into VLPs.
Figure 5B:
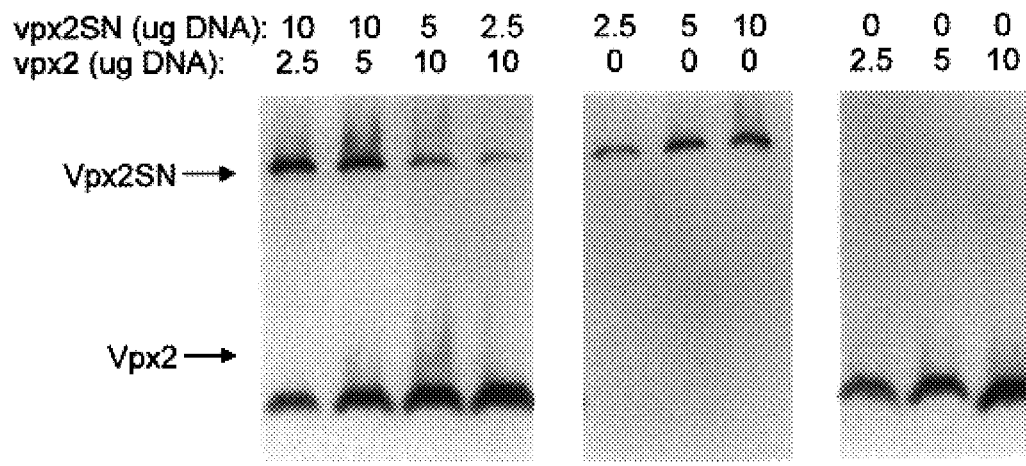

While Vpr1SN and Vpx2SN fusion proteins clearly associated with VLPs (FIG. 3), the question remained whether they would continue to do so in the presence of the native accessory proteins. The efficiency of Vpr1SN and Vpx2SN packaging was compared by competition analysis (FIG. 5). pTM-vpr1SN and pTM-vpx2SN were cotransfected with pTM-gag1/pTM-vpr1 and pTMgag2/pTM-vpx2, respectively, using ratios that ranged from 1:4 to 4:1 (FIG. 5A and FIG. 5B, left panels). For comparison, pTM-vpr1SN and pTM-vpr1were transfected individually with pTM-gag1 (FIG. 5A, middle and right panels respectively) and pTM-vpx2SN and pTM-vpx2 were transfected with pTM-gag2 (FIG. 5B, middle and right panels respectively). VLPs were pelleted through sucrose cushions, lysed, separated by PAGE, blotted onto nitrocellulose and probed with anti-SN antibody. The results revealed the presence of both Vpr1 and Vpr1SN in VLPs when cotransfected into the same cells (FIG. 5A, left panel). Similarly, coexpressed Vpx2 and Vpx2SN were also copackaged (FIG. 5B, left panel). Comparison of the relative amounts of VLP-associated Vpr1SN and Vpx2SN when expressed in the presence and absence of the native protein, indicated that there were no significant packaging differences. Thus, Vpr1/Vpx2 fusion proteins can efficiently compete with wild-type proteins for virion incorporation.

EXAMPLE 10

Vpr1SN and Vpx2SN Fusion Proteins Possess Nuclease Activity

To demonstrate that virion associated SN fusion proteins were enzymatically active, VLPs concentrated by ultracentrifugation from culture supernatants of HeLa cells transfected with pTM-gag1/pTM-vpr1SN and pTM-gag2/pTM-vpx2SN were analyzed for nuclease activity using an in vitro DNA digestion assay. Prior to this analysis, immunoblotting confirmed the association of Vpr1SN and Vpx2SN with VLPs (data not shown). FIG. 6 shows lambda phage DNA fragments in 0.8% agarose gels after incubation with dilutions of VLPs lysates that contained Vpr1- or Vpx2-SN fusion proteins. VLPs containing Vpr1SN* and Vpx2SN* were included as negative controls and dilutions of purified SN served as reference standards (FIG. 6A). Both virion associated Vpr1SN (FIG. 6B) and Vpx2SN (FIG. 6C) fusion proteins exhibited nuclease activity as demonstrated by degradation of lambda phage DNA. Cell-associated Vpr1SN and Vpx2SN fusion proteins also possessed nuclease activity when analyzed in this system (data not shown). To control for SN specificity, this analysis was also conducted in buffers devoid of $Ca^{++}$ and under these conditions no SN activity was detected (data not shown). Thus, SN remains enzymatically active when expressed as a fusion protein and packaged into VLPs.

EXAMPLE 11

Incorporation of Vpx2SN Fusion Protein into HIV-2 Virions

Figure 7B:
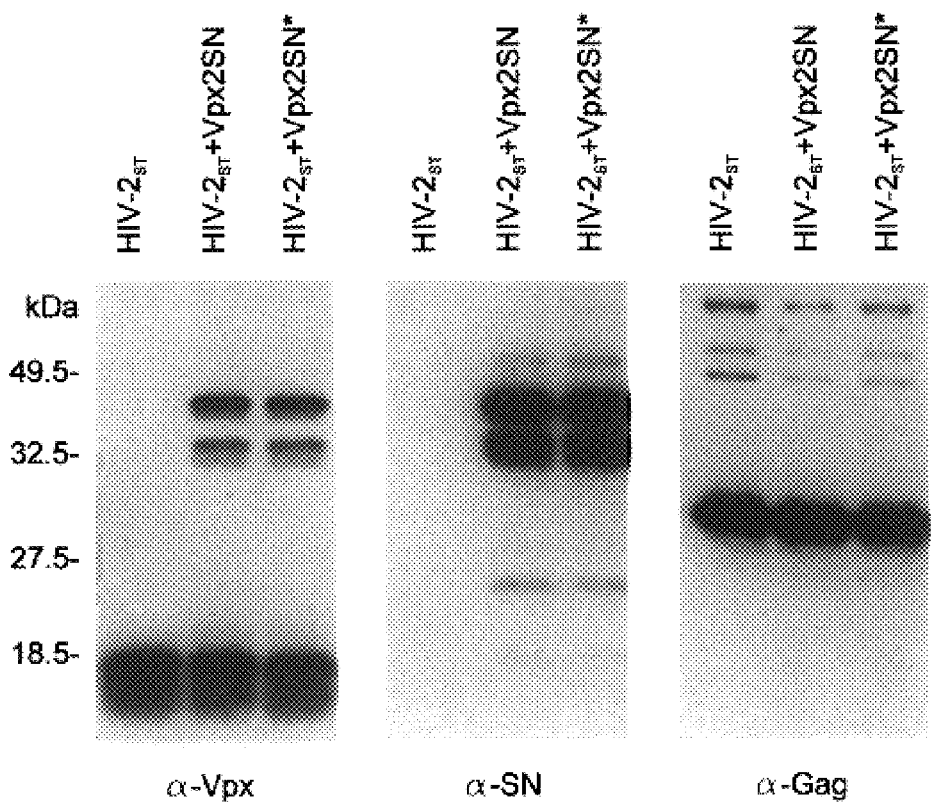

Vpx is incorporated into HIV-2 virions when expressed in trans. To show that Vpx2 fusion proteins were similarly capable of packaging into wild-type HIV-2 virions, an expression plasmid (pLR2P) was constructed placing the vpx2SN and vpx2SN* coding regions under control of HIV-2 LTR and RRE elements. The HIV-2 RRE was positioned downstream of the fusion genes to ensure mRNA stability and efficient translation (FIG. 7A). To show that the fusion proteins could package when expressed in trans, HIV-$2_{ST}$ proviral DNA (pSXBI) was transfected alone and in combination with pLR2P-vpx2SN and pLR2P-vpx2SN*. Forty-eight hours later, extracellular virus as pelleted from culture supernatants by ultracentrifugation through cushions of 20% sucrose and examined by immunoblot analysis (FIG. 7B). Duplicate blots were probed using anti-Vpx (left), anti-SN (middle) and anti-Gag (right) antibodies. Anti-Vpx antibody detected the 15 kDa Vpx2 protein in all viral pellets. In virions derived by cotransfection of HIV-$2_{ST}$ with pLR2P-vpx2SN and pLR2P-vpx2SN*, additional proteins of approximately 35 and 32 kDa were clearly visible. The same two proteins were also apparent on a duplicate blot probed with anti-SN antibodies, indicating that they represented Vpx2SN fusion proteins (FIG. 7B, middle panel). The predicted molecular weight of full-length Vpx2SN fusion protein is 33 kDa. As native Vpx and SN run slightly slower than predicted, it is likely that the 35 kDa species represents the full-length Vpx2SN fusion protein. Anti-SN antibodies detected additional proteins of approximately 21 and 17 kDa (these proteins were more apparent after longer exposure). Since only the 35 kDa protein was detected in Gag derived VLPs, which lack Pol proteins (FIG. 2), the smaller proteins represented cleavage products of Vpx2SN and Vpx2SN* generated by the viral protease. Anti-Gag antibodies confirmed the analysis of approximately equivalent amounts of virions from each transfection.

Figure 7C:
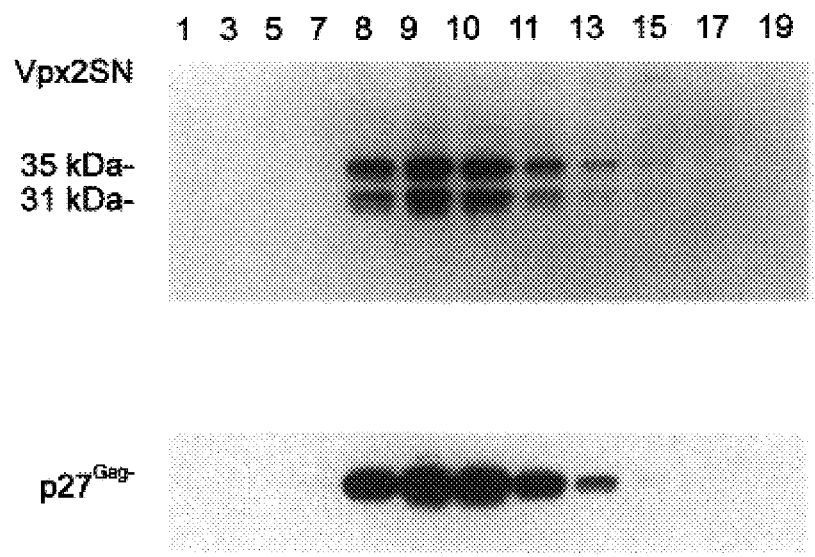

To show packaging of Vpx2SN into HIV-2 virions, sucrose gradient analysis was performed. Extracellular virus collected from culture supernatants of HLtat cells forty-eight hours after cotransfection with pLR2P-vpx2SN and HIV-$2_{ST}$ was pelleted through cushions of 20% sucrose. Pellets were resuspended in PBS and then centrifuged for 18 hours over linear gradients of 20–60% sucrose. Fractions were collected and analyzed by immunoblotting (FIG. 7C). Duplicate blots were probed separately with anti-SN (top) and anti-Gag (bottom) antibodies. Peak concentrations of both Vpx2SN and Gag were detected in fractions 8–11, demonstrating direct association and packaging of Vpx2SN into HIV-2 virions. These same sucrose fractions (8–11) were found to have densities between 1.16 and 1.17 g/ml, as determined by refractometric analysis (data not shown). Again, both the 35 kDa and 32 kDa forms of Vpx2SN were detected, providing further evidence for protease cleavage following packaging into virus particles.

Figure 7D:
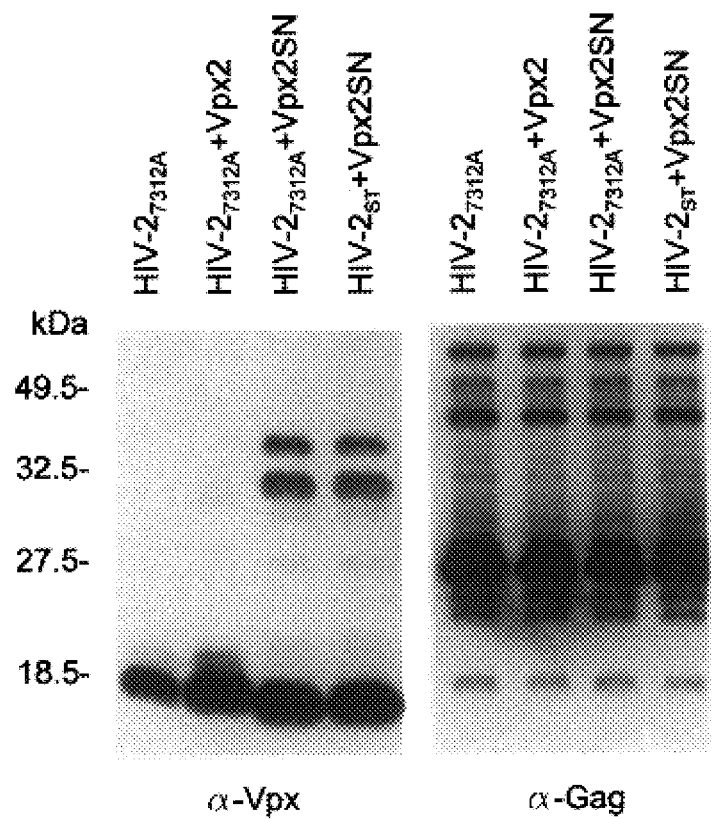

Since HIV-$2_{ST}$ is defective in vpr, this may have affected the packaging of the Vpx2SN fusion protein. A second strain of HIV-2, termed HIV-$2_{7312A}$, was analyzed which was cloned from short-term PBMC culture and contains open reading frames for all genes, including intact vpr and vpx genes (unpublished). A plasmid clone of HIV-2$_{7312A}$ proviral DNA (pJK) was transfected alone and in combination with pLR2P-vpx2SN into HLtat cells. For comparison, HIV-2$_{ST}$ was also co-transfected with pLR2P-vpx2SN. Progeny virus was concentrated by ultracentrifugation through sucrose cushions and examined by immunoblot analysis (FIG. 7D). Duplicate blots were probed with anti-Vpx (left) and anti-Gag (right) antibodies. The results revealed comparable levels of Vpx2SN incorporation into vpr competent virus (HIV-2$_{7312A}$) compared with vpr-defective virus (HIV-2$_{ST}$). Moreover, the 35 kDa and 32 kDa proteins were again detected in HIV-2$_{7312A}$ virions. Thus, efficient incorporation of the Vpx2SN protein into replication-competent wild-type HIV-2 was demonstrated, even in the presence of native Vpr and Vpx proteins.

EXAMPLE 12
Incorporation of Vpr1SN into HIV-1 Virions

Figure 8A:
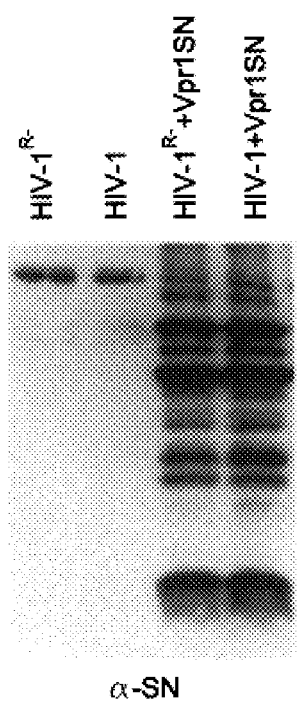
FIGS. 8A–C show the incorporation of Vpr1SN into HIV-1 virions by trans complementation. Culture supernatant virus from HLtat cells transfected with pNL4-3 (HIV-1) and pNL4-3R$^-$ (HIV-1 vpr mutant) or cotransfected with pNL4-3/pLR2P-vpr1SN and pNL4-3R$^{31}$/pLR2P-vpr1SN was prepared for immunoblot analysis as described above. Blots were probed with anti-SN (FIG. 8A), anti-Vpr1 (FIG. 8B) and anti-Gag (FIG. 8C) antibodies.
Figure 8B:
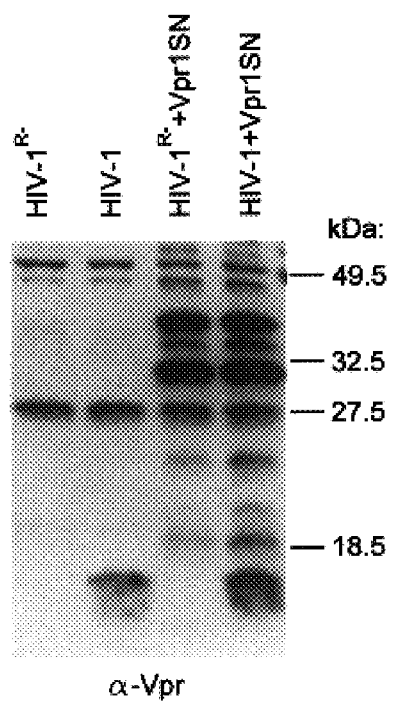
Figure 8C:
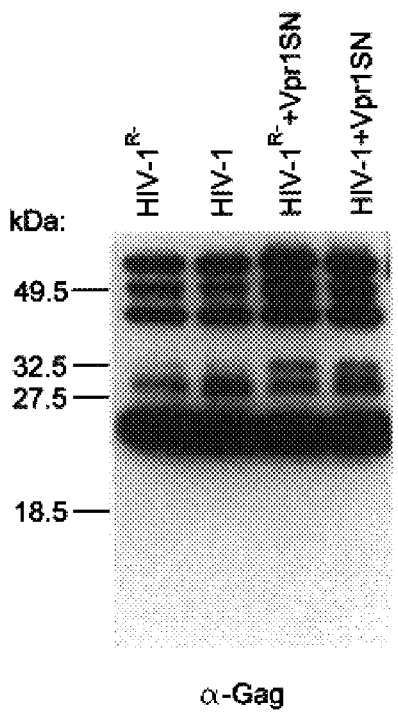

Using the same LTR/RRE-based expression plasmid, it was also shown that Vpr1SN could package into HIV-1 virions by co-expression with HIV-1 provirus (as discussed above, the HIV-2 LTR can be transactivated by HIV-1 Tat and the HIV-2 RRE is sensitive to the HIV-1 Rev protein). Virions released into the culture medium 48 hours after transfection of HLtat cells with pNL4-3 (HIV-1) and pNL4-3-R⁻ (HIV-1-R⁻) alone and in combination with pLR2P-vpr1Sn were concentrated by ultracentrifugation and examined by immunoblot analysis (FIG. 8). As observed in cotransfection experiments with HIV-2, anti-SN antibodies identified two major Vpr1SN fusion proteins of approximately 34 to 31 kDa. These proteins were not detected in virions produced by transfection of pNL4-3 and pNL4-e-R⁻ alone. From expression in the rVT7 system, the full-length Vpr1SN fusion protein was expected to migrate at 34 kDa. Therefore, the 31 kDa protein likely represents a cleavage product. Anti-SN antibodies also detected a protein migrating at 17 kDa. Anti-Vpr antibody detected the 34 and 31 kDa proteins in virions derived from cotransfected cells. It is noteworthy that both the anti-Vpr and anti-SN antibodies detected the 31 kDa protein most strongly, and that anti-Vpr antibody did not detect the 17 kDa protein recognized by anti-SN antibody. These results also show that even in virions in which native Vpr protein was packaged, Vpr1SN was also incorporated in abundance. Gag monoclonal antibody detected similar amounts of Gag protein in all viral pellets and demonstrated processing of the p55$^{Gag}$ precursor (FIG. 8C).

To demonstrate more directly that cleavage of the Vpr1- and Vpx2-SN fusion proteins was mediated by the HIV protease, virus was concentrated from pNL4-3-R⁻/pLR2P-vpr1SN and pSXB1/pLR2P-vpx2SN transfected cells that were culture in the presence of 1 μM of the HIV protease inhibitor L-689,502 (provided by Dr. E. Emini, Merck & Co. Inc.). As expected, immunoblot analysis of virions demonstrated substantially less processing of p55$^{Gag}$ (FIG. 9A). Similarly, virions produced in the presence of L-689,502 also contained greater amounts of the uncleaved species of Vpr1SN and Vpx2SN fusion proteins (FIG. 9B). Taken together, these results demonstrate that Vpr1- and Vpx2-SN fusion proteins are subject to protease cleavage during or subsequent to virus assembly.

EXAMPLE 13
Vpr1-CAT and Vpr 2-CAT Fusion Protein Incorporation into HIV Virions

Figure 10A:
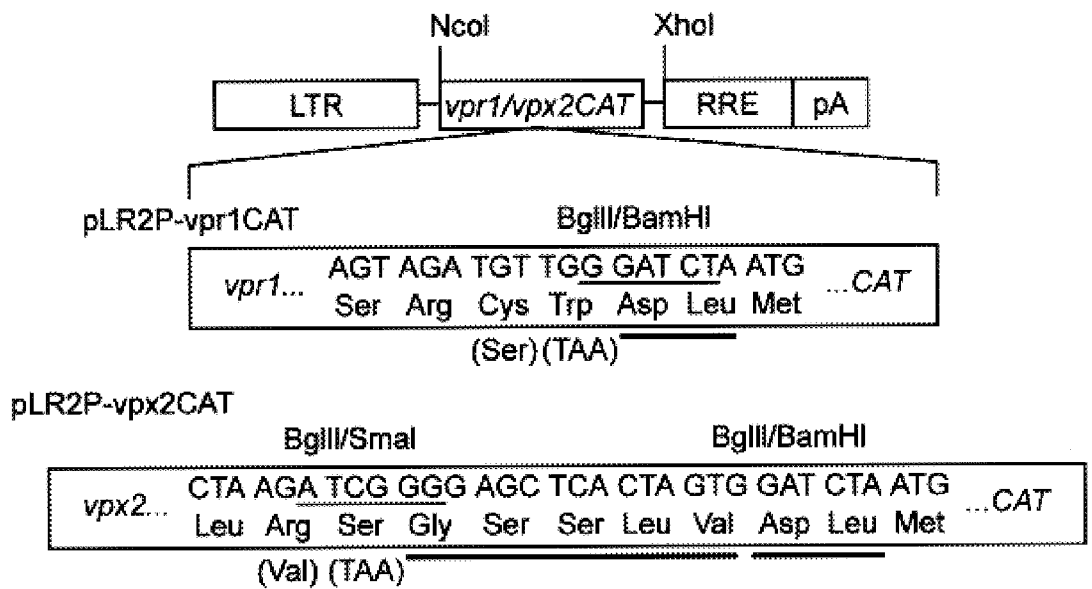
FIGS. 10A and 10B show the incorporation of enzymatically active Vpr1- and Vpx2-CAT fusion proteins into HIV virions.
Figure 10B:
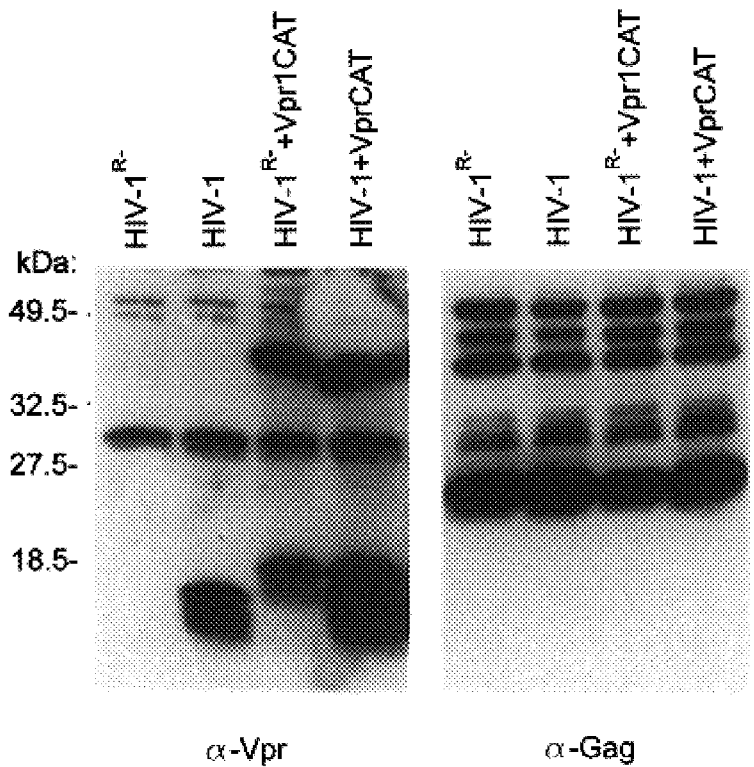
Figure 10C:
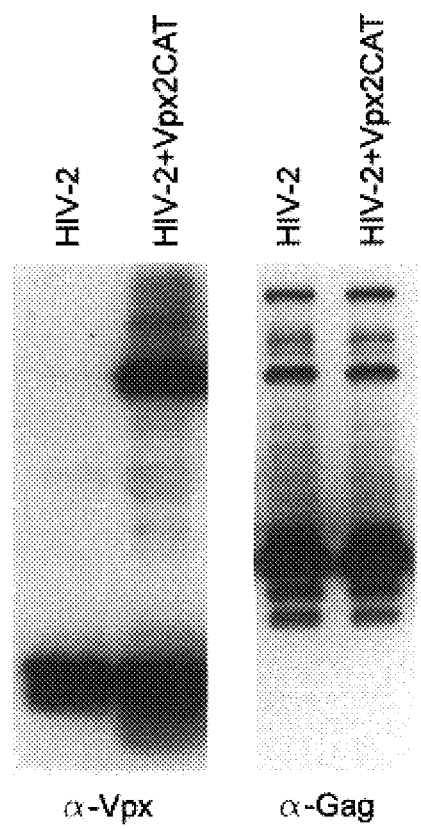
FIG. 10C shows the incorporation of Vpx2CAT into HIV-2 virions. Virus produced from HLtat cells transfected with pSXB1 (HIV-2) or cotransfected with pSXB1/pLR2P-vpx2CAT was prepared as described above and examined by immunoblot analysis. Replica blots were probed with anti-Vpx2 (left) and anti-Gag (right) antibodies.

To show that Vpx2 and Vpr1 could target additional proteins to the HIV particle, the entire 740 bp CAT gene was substituted for SN in the pLR2P-vpx2SN and pLR2P-vpr1SN vectors, generating pLR2P-vpr1CAT and pLR2P-vpx2CAT (FIG. 10A). pNL4-3/pLR2P-vpr1CAT, pnl4-3-R⁻/pLR2P-vpr1CAT and pSXB1/pLR2P-vpx2CAT were co-transfected into HLtat cells. As controls, pNL4-3, pNL4-3-R⁻ and pSXB1 were transfected alone. Progeny virions, concentrated from culture supernatants, were analyzed by immunoblotting (FIG. 10B and 10C). Using anti-Vpr antibodies, 40 kDa fusion proteins were detected in viral pellets derived by co-transfection of pRL2P-vpr1CAT with both pNL4-3 and pNL4-3-R⁻ (FIG. 10B). This size is consistent with the predicted molecular weight of the full-length Vpr1CAT fusion protein. In addition, anti-Vpr antibodies also detected a 17 kDa protein which did not correspond to the molecular weight of native Vpr1 protein (14.5 kDa in virions derived from cells transfected with pNL4-3). The same protein was recognized weakly with anti-CAT antibodies, suggesting a fusion protein cleavage product containing most Vpr sequence. Very similar results were obtained with virions derived from HLtat cells co-transfected with HIV-2$_{ST}$ and pRL2P-vpx2CAT, in which anti-Vpx antibody detected 41 and 15 kDa proteins (FIG. 10C). These results demonstrate that Vpr1CAT and Vpx2CAT fusion proteins are packaged into virions. However, like in the case of SN fusion proteins, CAT fusion proteins were also cleaved by the HIV protease (the Vpx2CAT cleavage product is not visible because of co-migration with the native Vpx protein). CAT cleavage appeared less extensive, based on the intensity of the full-length CAT fusion protein on immunoblots.

Figure 10D:
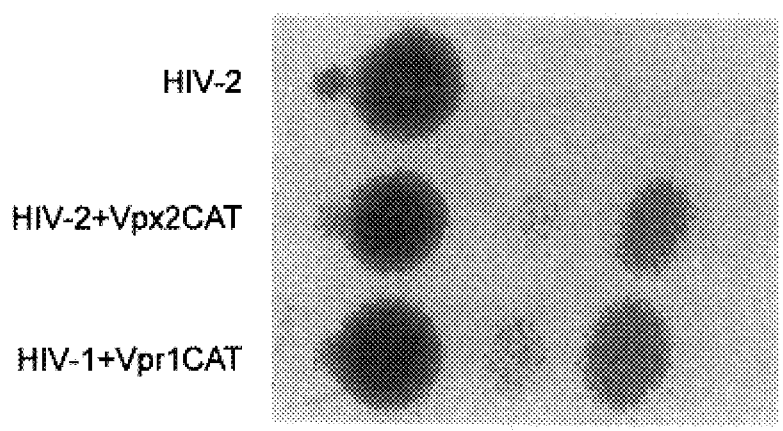
FIG. 10D shows that virion incorporated Vpr1- and Vpx2-CAT fusion proteins possess enzymatic activity. Viruses pelleted from HLtat cells transfected with pSXB1 (HIV-2) or cotransfected with pSXB1/pLR2P-vpx2CAT and pNL4-3/pLR2P-vpr1CAT were lysed and analyzed for CAT activity. HIV-2 was included as a negative control.

Lysates of HIV-1 and HIV-2 viral particles were diluted 1:50 in 20 mM Tris-base and analyzed for CAT activity by the method of Allon, et al., Nature 282:864–869 (1979). FIG. 10D indicates that virions which contained Vpr1 CAT and Vpx2CAT proteins possessed CAT activity. These results show the packaging of active Vpr1- and Vpx2-CAT fusion proteins.

Figure 11A:
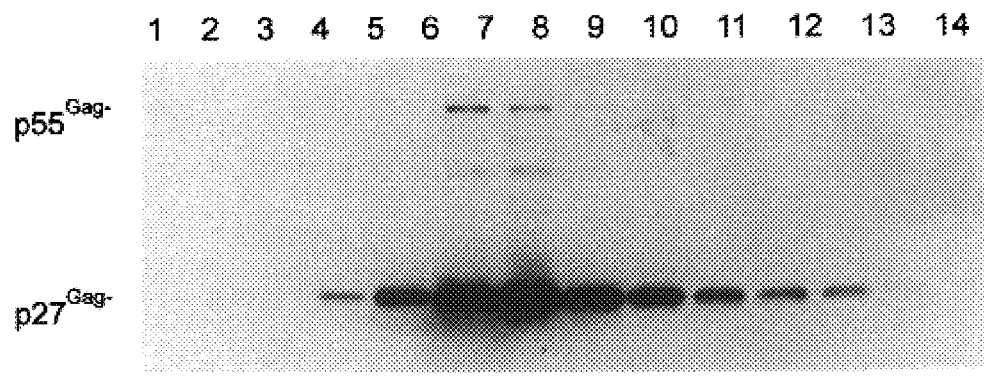
FIGS. 11A–D show virion association of enzymatically active CAT and SN fusion proteins.
Figure 11B:
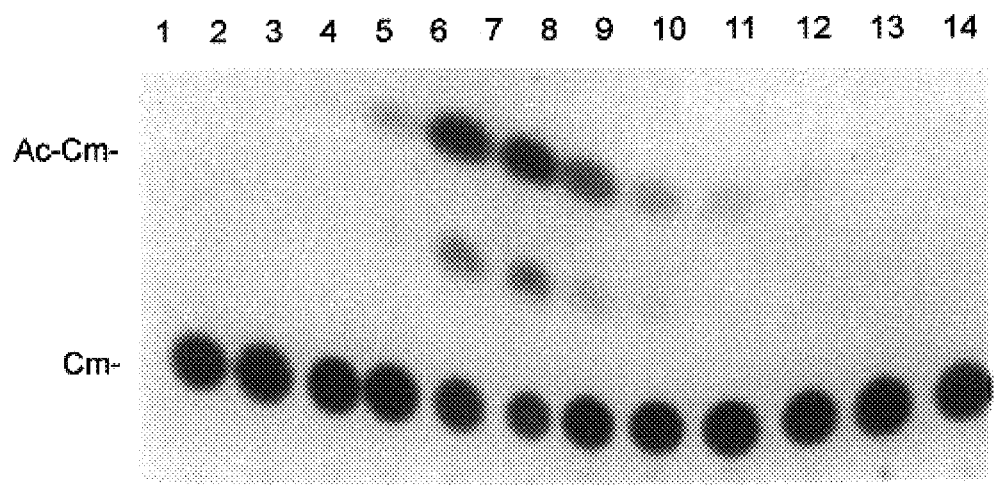

EXAMPLE 14
Virion Incorporated SN and CAT Fusion Proteins are Enzymatically Active The ability of Vpr1 and Vpx 2 to deliver functionally active proteins to the virus particle was further confirmed by sucrose gradient analysis. Virions derived from HLtat cells co-transfected with HIV-2$_{ST}$ and pLR2P-vpx2 were sedimented in linear gradients of 20–60% sucrose as described above. Fractions were collected and analyzed for viral Gag protein (FIG. 11A) and corresponding CAT activity (FIG. 11B). Peak amounts of Gag protein were detected in fractions 6 and 7 (density 1.16 and 1.17, respectively). Similarly, peak amounts of acetylated chloramphenicol (Ac-cm) were also detected in fractions 6 and 7.

Figure 11C:
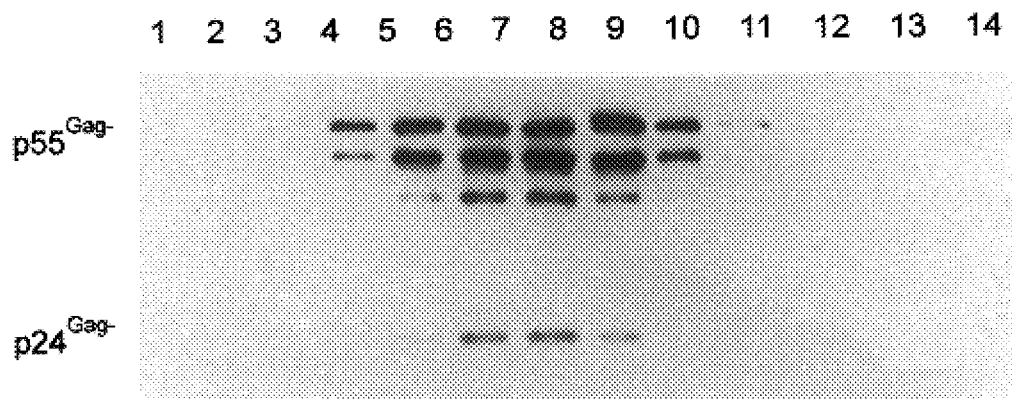
Figure 11D:
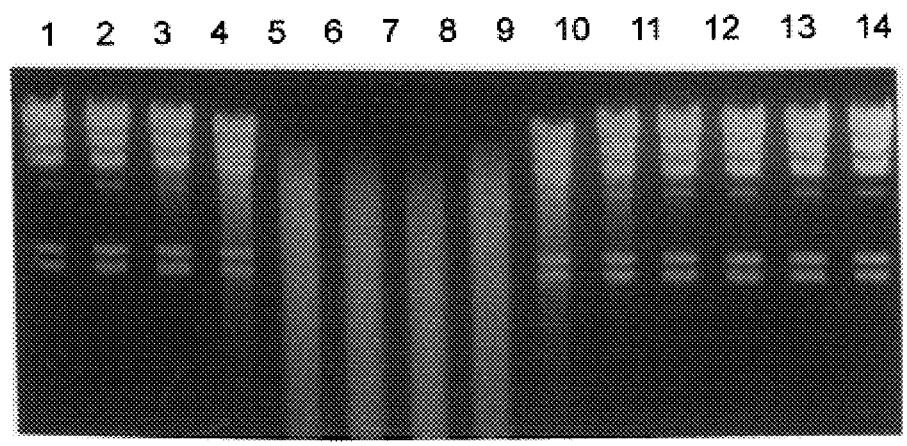

Whether virion associated SN fusion protein retained nuclease activity was also shown. HIV-1$_{SG3}$ virions containing Vpr1SN were analyzed after sedimentation in linear gradients of sucrose (FIG. 11). Since the present invention demonstrated that protease cleavage of SN fusion proteins (FIGS. 7, 8 and 9) markedly reduced Vpr1SN nuclease activity (data not shown), these experiments were performed by culturing pSG3/pLR2P-vpr1SN co-transfected cells in the presence of L-689,502 as described above. Immunoblot analysis of sedimented virions revealed peak concentrations of Gag in fractions 6 and 7 and substantially reduced p55 processing (FIG. 11C). Peak SN activity was associated with the fractions that contained the highest concentrations of virus (FIG. 11D). These results thus document that virion incorporation per se does not abrogate the enzymatic activity of Vpr/Vpx fusion proteins, although cleavage by the viral protease may inactivate the fusion partners.

The present invention demonstrated the capability of HIV-1 Vpr and HIV-2 Vpx to direct the packaging of foreign proteins into HIV virions when expressed as heterologous fusion molecules. The trans complementation experiments with HIV proviral DNA revealed that Vpr1 and Vpx2 fusion proteins were also incorporated into replication-competent viruses. Moreover, packaging of the fusion proteins in the presence of wild-type Vpx and/or Vpr proteins (FIGS. 5, 7 and 8) indicated that the viral signals mediating their packaging were not obstructed by the foreign components of the fusion molecules. Likewise, virion-associated SN and CAT fusion proteins remained enzymatically active.

Based on the immunoblot analysis of VLPs and virions, the present invention illustrates that both virion associated CAT and SN/SN* are susceptible to cleave by the viral protease. There appears to be at least one cleavage site in CAT and two cleavage sites in the SN/SN* proteins. Based on calculated molecular weights of the major SN/SN* cleavage products, it appears that SN and SN* are cleaved once near their C termini and once near the fusion protein junctions. Since the fusion protein junctions of Vpr1SN and Vpx2SN are not identical it is also possible that these regions differ with respect to their susceptibility to the viral protease. Although Vpx2SN/SN* were processed to a lesser extent than Vpr1SN (FIGS. 7 an 8), the major cleavage sites appear to be conserved. There is no doubt that both the HIV-1 and HIV-2 proteases recognize processing sites in the fusion partners and that there is sufficient physical contact to enable cleavage. This is evidenced both by the reduction of cleavage product intensities on immunoblots as well as by an increased enzymatic activity in the presence of an HIV protease inhibitor.

The demonstration that Vpr1 and Vpx2 fusion proteins are capable of associating with both VLPs and virions facilitates studies on these accessory proteins and on HIV assembly in general. The approach of generating deletion mutants to study protein structure/function relationships is often of limited value since this can reduce protein stability or change the three-dimensional structure of the protein. In the case of Vpr, a single amino acid substitution at residue 76 has been shown to destabilize its expression in infected cells. Studies have indicated that deletion mutations in vpr and vpx result in premature degradation of the proteins following expression. Fusion of Vpr and Vpx mutant proteins with, e.g., SN or CAT as demonstrated by the present invention, increase stability.

The successful packaging of Vpr1/Vpx2SN fusion proteins into virions indicates their use for accessory protein targeted viral inactivation. The present invention demonstrates that Vpr and Vpx may serve as vehicles for specific targeting of virus inhibitory molecules, including SN. In contrast to HIV Gag, Vpr and Vpx are small proteins that can be manipulated relatively easily without altering virus replication and thus may represent vehicles with considerable versatility for application to such an antiviral strategy.

The present invention demonstrated that Vpr and Vpx can serve as vehicles to deliver functionally active enzymes to the HIV virion, including those that may exert an antiviral activity such as SN. The present invention has demonstrated that the concept of accessory protein targeted virus inactivation is feasible.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method for generating a viral vector particle comprising a viral fusion protein, said method comprising:
   a) providing to a mammalian cell a DNA sequence encoding said viral fusion protein operably linked to a promoter active in said cell, said fusion protein comprising at least a first and a second amino acid sequence, said first amino acid sequence comprising at least a fragment of a retroviral Vpr amino acid sequence wherein said fragment is capable of being packaged into the viral vector particle, said second amino acid sequence possessing an enzymatic activity;
   b) providing to said mammalian cell at least one nucleic acid sequence of a retrovirus, said nucleic acid sequence encoding at least a Gag protein, wherein said retroviral nucleic acid sequence is expressed in said cell; and, c) forming from said cell said viral vector particles.

2. The method according to claim 1 wherein said amino acid sequence comprising the retroviral Vpr is obtained from HIV or SIV.

3. The method according to claim 1 wherein said second amino acid sequence is other than a sequence obtained from Vpx.

4. The method according to claim 1 wherein said second amino acid sequence comprises a polypeptide selected from the group consisting of staphylococcal nuclease, chloramphenicol acetyl transferase, an amino acid sequence that can degrade viral nucleic acid, a marker/reporter protein, a functional enzyme, and a virus inhibitory protein.

5. The method according to claim 1 wherein said second amino acid sequence is obtained from HIV or SIV and comprises a polypeptide selected from the group consisting of protease, integrase, reverse transcriptase, vif, nef, and gag.

6. The method according to claim 1 wherein said viral fusion protein is expressed in trans to gag.

7. The method according to claim 1 wherein said viral particle comprises at least said viral fusion protein and a Gag protein.

8. The method of claim 1, wherein said viral vector particle further comprises at least one of the group consisting of a viral envelope protein and a viral nucleic acid sequence.

9. The method of claim 1, wherein said method further comprises isolating said viral vector particles.

10. The method of claim 1, wherein said mammalian cell further comprises a second nucleic acid sequence, said second nucleic acid sequence encoding an envelope protein.

11. A method for generating a viral vector particle comprising a viral fusion protein, said method comprising:
   a) providing to a mammalian cell a DNA sequence encoding said viral fusion protein operably linked to a promoter active in said cell, said fusion protein comprising at least a first and a second functional amino acid sequence, said first amino acid sequence comprising at least a fragment of a retroviral Vpr amino acid sequence wherein said fragment is capable of being packaged into the viral vector particle;
   b) providing to said mammalian cell at least one nucleic acid sequence of a retrovirus, said nucleic acid sequence encoding at least a Gag protein, wherein said retroviral nucleic acid sequence is expressed in said cell; and,
   c) forming from said cell said viral vector particles.

12. A method for generating a viral vector particle comprising a viral fusion protein, said method comprising:
   a) providing to a mammalian cell a DNA sequence encoding said viral fusion protein operably linked to a promoter active in said cell, said fusion protein comprising at least a first and a second amino acid sequence, said first amino acid sequence comprising at least a fragment of a retroviral Vpx amino acid sequence wherein said fragment is capable of being packaged into the viral vector particle;
   b) providing to said mammalian cell at least one nucleic acid sequence of a retrovirus, said nucleic acid sequence encoding at least a Gag protein, wherein said retroviral nucleic acid sequence is expressed in said cell; and,
   c) forming from said cell said viral vector particles.

13. The method of claim 12 further comprising isolating the viral vector particle.

14. The method of claim 12, wherein said mammalian cell further comprises a second nucleic acid sequence, said second nucleic acid sequence encoding an envelope protein.

15. The method of claim 12, wherein said second amino acid sequence encodes an enzymatically active polypeptide.

16. The method of claim 12 wherein said amino acid sequence comprising the retroviral Vpx is obtained from HIV or SIV.

17. The method of claim 12 wherein said second amino acid sequence encodes a polypeptide selected from the group consisting of staphylococcal nuclease, chloramphenicol acetyl transferase, an amino acid sequence that can degrade viral nucleic acid, a marker/reporter protein, a functional enzyme, and a virus inhibitory protein.

18. The method of claim 15 wherein said second amino acid sequence is obtained from HIV or SIV and encodes a polypeptide selected from the group consisting of protease, integrase, reverse transcriptase, vif, nef, and gag.

19. The method of claim 12 wherein said viral fusion protein is expressed in trans to gag.

20. The method of claim 12 wherein said viral particle comprises at least said viral fusion protein and a Gag protein.

21. The method of claim 20, wherein said viral vector particle further comprises at least one of the group consisting of a viral envelope protein and a viral nucleic acid sequence.

22. A method for generating a viral vector particle comprising a viral fusion protein, said method comprising:
   a) providing to a mammalian cell a DNA sequence encoding said viral fusion protein operably linked to a promoter active in said cell, said fusion protein comprising a first and a second amino acid sequence, said first amino acid sequence comprising at least a fragment of a retroviral Vpr or Vpx amino acid sequence wherein said fragment is capable of being packaged into the viral vector particle and said second amino acid sequence comprises reverse transcriptase;
   b) providing to said mammalian cell at least one nucleic acid sequence of a retrovirus, said nucleic acid sequence encoding at least a Gag protein and an envelope protein, wherein said retroviral nucleic acid sequence is expressed in said cell; and,
   c) forming from said cell said viral vector particles.

23. A method for generating a viral vector particle comprising a viral fusion protein, said method comprising:
   a) providing to a mammalian cell a DNA sequence encoding said viral fusion protein operably linked to a promoter active in said cell, said fusion protein comprising a first and a second amino acid sequence, said first amino acid sequence comprising at least a fragment of a retroviral Vpr or Vpx amino acid sequence wherein said fragment is capable of being packaged into the viral vector particle and said second amino acid sequence comprises integrase;
   b) providing to said mammalian cell at least one nucleic acid sequence of a retrovirus, said nucleic acid sequence encoding at least a Gag protein, wherein said retroviral nucleic acid sequence is expressed in said cell; and,
   c) forming from said cell said viral vector particles.

* * * * *

UNITED STATES PATENT AND TRADEMARK OFFICE
CERTIFICATE OF CORRECTION

PATENT NO.    : 6,362,000 B1
DATED         : March 26, 2002
INVENTOR(S)   : Kappes et al.

It is certified that error appears in the above-identified patent and that said Letters Patent is hereby corrected as shown below:

<u>Title page,</u>
Item [*] Notice: "This patent issued on a continued prosecution application filed under 37 CFR 1.53(d)," should read -- This patent issued resulting from a Request for Continued Examination (RCE) under 37 CFR 1.114, --.

<u>Column 8,</u>
Line 31, "SEQ ID NO:6" should read -- SEQ ID NO:5 --;
Line 32, after "C-3" insert -- SEQ ID NO:6 --;
Line 39, before the prime notation (') insert -- 3 --.

<u>Column 20,</u>
Line 17, "claim 15" should read -- claim 12 --.

Signed and Sealed this

Twenty-ninth Day of October, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO. : 6,362,000 B1
DATED : March 26, 2002
INVENTOR(S) : Kappes et al.

It is certified that error appears in the above-identified patent and that said Letters Patent is hereby corrected as shown below:

<u>Title page,</u>
Item [73], Assignee, "University of Alabama Research Foundation" should read
-- UAB Research Foundation --.

Signed and Sealed this

Fifteenth Day of June, 2004

JON W. DUDAS
*Acting Director of the United States Patent and Trademark Office*

SEQUENCE LISTING

<160> NUMBER OF SEQ ID NOS: 10

<210> SEQ ID NO 1
<211> LENGTH: 27
<212> TYPE: DNA
<213> ORGANISM: HIV virus

<400> SEQUENCE: 1
gccacctttg tcgactgtta aaaaact        27

<210> SEQ ID NO 2
<211> LENGTH: 24
<212> TYPE: DNA
<213> ORGANISM: HIV virus

<400> SEQUENCE: 2
gtcctaggca agcttcctgg atgc           24

<210> SEQ ID NO 3
<211> LENGTH: 25
<212> TYPE: DNA
<213> ORGANISM: HIV virus

<400> SEQUENCE: 3
aaggagacgg atgggtgcga gagcg          25

```
<210> SEQ ID NO 4
<211> LENGTH: 26
<212> TYPE: DNA
<213> ORGANISM: HIV virus

<400> SEQUENCE: 4
ggggatccct ttattgtgac gagggg                                              26

<210> SEQ ID NO 5
<211> LENGTH: 25
<212> TYPE: DNA
<213> ORGANISM: HIV virus

<400> SEQUENCE: 5
attgtgggcc atgggcgcga gaaac                                               25

<210> SEQ ID NO 6
<211> LENGTH: 24
<212> TYPE: DNA
<213> ORGANISM: HIV virus

<400> SEQUENCE: 6 gggggggcccc tactggtctt ttcc                                               24

<210> SEQ ID NO 7
<211> LENGTH: 28
<212> TYPE: DNA
<213> ORGANISM: HIV virus

<400> SEQUENCE: 7
gaagatctac catggaagcc ccagaaga                                            28

<210> SEQ ID NO 8
<211> LENGTH: 39
<212> TYPE: DNA
<213> ORGANISM: HIV virus

<400> SEQUENCE: 8
cgcggatccg ttaacatcta ctggctccat ttcttgctc                                39

<210> SEQ ID NO 9
<211> LENGTH: 25
<212> TYPE: DNA
<213> ORGANISM: HIV virus

<400> SEQUENCE: 9
gtgcaacacc atggcaggcc ccaga                                               25

<210> SEQ ID NO 10
<211> LENGTH: 39
<212> TYPE: DNA
<213> ORGANISM: HIV virus

<400> SEQUENCE: 10
tgcactgcag gaagatctta gacctggagg gggaggagg                                39
```